United States Patent
Jones et al.

(10) Patent No.: US 9,550,764 B2
(45) Date of Patent: Jan. 24, 2017

(54) FUSED HETEROCYCLIC COMPOUNDS AND THEIR USE

(71) Applicant: The Institute of Cancer Research: Royal Cancer Hospital, London, Greater London (GB)

(72) Inventors: Keith Jones, Sutton (GB); Matthew David Cheeseman, Sutton (GB); Spyridon Linardopoulos, Sutton (GB); Amir Faisal, Sutton (GB); Olivier Remi Barbeau, Sutton (GB); Andrew Kalusa, Sutton (GB)

(73) Assignee: The Institute of Cancer Research: Royal Cancer Hospital (GB)

( * ) Notice: Subject to any disclaimer, the term of this patent is extended or adjusted under 35 U.S.C. 154(b) by 0 days.

(21) Appl. No.: 14/421,503

(22) PCT Filed: Aug. 22, 2013

(86) PCT No.: PCT/GB2013/052213
§ 371 (c)(1),
(2) Date: Feb. 13, 2015

(87) PCT Pub. No.: WO2014/030001
PCT Pub. Date: Feb. 27, 2014

(65) Prior Publication Data
US 2015/0232462 A1 Aug. 20, 2015

Related U.S. Application Data

(60) Provisional application No. 61/692,321, filed on Aug. 23, 2012.

(51) Int. Cl.
| C07D 417/10 | (2006.01) |
|---|---|
| C07D 417/14 | (2006.01) |
| C07D 417/04 | (2006.01) |
| C07D 413/04 | (2006.01) |

(52) U.S. Cl.
CPC ........... *C07D 417/14* (2013.01); *C07D 413/04* (2013.01); *C07D 417/04* (2013.01)

(58) Field of Classification Search
CPC .................................................. C07D 417/10
USPC ......................................... 548/181; 514/365
See application file for complete search history.

(56) References Cited

U.S. PATENT DOCUMENTS 5,643,932 A * 7/1997 Chihiro ................ C07D 277/24
514/342

FOREIGN PATENT DOCUMENTS

WO 2009033033 A2 3/2009

OTHER PUBLICATIONS

Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Invanisevic et al. "Use of X-ray . . . " Pharm. Sci. Encycl. p. 1-42 (2010).*
Bhattacharya excerpt fr Brittain, H. ed., Polymorphism in Pharmaceutical SolidsDrugs and the Pharmaceutical Sciences ; V. 95 New York Marcel Dekker, Inc., 1999.*
Ivanisevic, I. Pharm. Form. Qual. 2011, pp. 30-33.*
Kirk-Othmer "Crystallization" Encyclopedia of Chem. Tech. v. 8, p. 95-147 (2002).*
Seddon "Pseudopolymorph . . . " Crystal Growth & design v.4(6) p. 1087 (2004) (2 pages from internet).*
Ala et al., 2012, "The oncogenic phospitatase PPM1D confers cisciatin resistance in evanan carcinoma cells by attenuating checkpoint kinase 1 and p53 activation", Oncogene, vol. 31. No, 17, pp. 2175-2186.
Boys et al., 2006, "Preparation of primaiy thioamides from nitriles using sodium hydrogen sulfide and diethylamine hydrochloride", Synthetic Communications, vol. 35, No. 3, p. 295-296.
Bulavin et al., 2002, "Amplification of PPM1D in human tumors abrogates p53 tumor-suppressor activity", Nature Genetics., vol. 31, pp. 210-215.
Bulavin et at., 2004, "Inactivatlon of the Wip1 phosphatase inhibits mammary tumorigenesis through p38 MAPK-mediated activation of the p16(Ink4a)-p19(Arf) pathway", Nature Genetics, vol. 36, pp. 343-350.
Castellino et al., 2008, "Medulloblastomas overexpress the p53-inactivating oncogene WIP1/PPM1D", J. Neuro-oncol., vol. 86, pp. 245-256.
Emelyanov et al., 2014, "Wip1 phosphatase in breast cancer", Oncogene, pp. 1-10.

(Continued)

*Primary Examiner* — Patricia L Morris
(74) *Attorney, Agent, or Firm* — Tarolli, Sundheim, Covell & Tummino LLP

(57) ABSTRACT

The present invention provides compounds of formula (I) and pharmaceutically acceptable salts, hydrates and solvates thereof for use in the treatment of cancer:

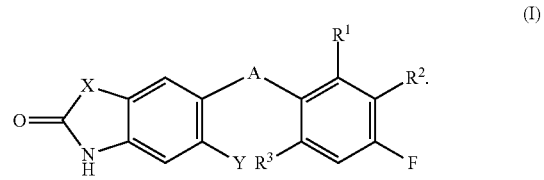

13 Claims, 1 Drawing Sheet

(56) References Cited

OTHER PUBLICATIONS

Fiscella et al., 1997, "Wip1, a novel human protein phosphatase that is induced in response to ionizing radiation in a p53-dependent manner", Proc. Natl. Acad. Sci. USA, vol. 94, pp. 6048-6053.
Fujimoto et al., 2006, "Regulation of the antioncogenic Chk2 kinase by the oncogenic Wip1 phosphatase,"Cell Death Differ., vol. 13, pp. 1170-1180.
Hu et al., 2009, "Genetic alterations and oncogenic patways associated with breast cancer subtypes", Mol. Cancer Res., vol. 7, pp. 511-522.
Kamisuki et al., 2011, "Synthesis and evaluation of diarylthiazole derivatives that inhibit activatin of sterol regulatory element-binding proteins", J. Med. Chem., vol. 54, No. 13, pp. 4923-4927.
Lambros et al., 2010, "PPM1D overexpression and gene amplification in breast cancers:qRT-PCR and chromogenic in situ hybridisation study", Modern Pathology, vol. 23, No. 10, pp. 1334-1345.
Lammers et al., 2007, "Role of Type 2C Protein Phosphatases in Growth Regulation and in Cellular Stress Signaling", Crit. Rev. Biochem. Mol. Bio., vol. 42, pp. 437-461.
Liu et al., 2014, "Overexpression of Wip1 is associated with biologic behavior in human clear cell renal cell carcinoma", PLOS ONE, vol. 9, No. 10, e110218, pp. 1-10.
Loukopoulos et al., 2007, "Genome-wide array-based comparative genomic hybridization analysis of pancreatic adenocarcinoma identification of genetic indicators that predict patient outcome", Cancer Sci., vol. 98, pp. 392-400.
Lu et al., 2004, "The p53-Induced Oncogenic Phosphatase PPM1D Interacts with Uracil DNA Glycosylase and Suppresses Base Excision Repair", Mol. Cell. vol. 15, pp. 621-634.
Lu et al., 2005, "PPM1D dephosphorylates Chk1 and p53 and abrogates cell cycle checkpoints", Gebes Dev., vol. 19, pp. 1162-1174.
Manaka et al., 2005, "Synthesis of aromatic thioamide from nitrile without handling of gaseous hydrogen sulfide", Synthetic Communications, vol. 35, No. 5, pp. 761-764.
Miyashita et al., 2003, "Total synthesis of (+/−)-spiroxin C", Organic Letters, vol. 5, No. 15, pp. 2683-2686.
Nannenga et al., 2006, "Augmented cancer resistance and DNA damage response phenotypes in PPM1D null mice", Mol. Carcinog., vol. 45, pp. 594 604.
Natrajan et al., 2009, "Tiling path genomic profiling of grade 3 invasive ductal breast cancers". Clin. Cancer Res., vol. 15, pp. 2711-2722.
Natrajan et al., 2010, "An integrative genomic and transcriptomic analysis reveals molecular pathways and networks regulated by copy number aberrations in basal-like, HER2 and luminal cancers", Breast Cancer Res. Treat., vol. 121, pp. 575-589.
Oliva-Trastoy et al., 2007, "The Wip1 phosphatase (PPM1D) antagonizes activation of the Chk2 tumour suppressor kinase", Oncogene. vol. 26, pp. 1449 1458.
Proia et al., 2006, "Dual Roles for the Phosphatase PPM1D in Regulating Progesterone Receptor Funtion", J. Biol. Chem., vol. 281, pp. 7089-7101.
Saito-Ohara et al., 2003, "PPM1D is a potential target for 17q gain in neuroblastoma", Cancer Res., vol. 63, pp. 1876-1863.
Sheeram et al., 2006, "Wip1 phosphatase modulates ATM-dependent signaling pathways", Mol. Cell, vol. 23, No. 5, pp. 757-764.
Takekawa et al., 2000, "p53-inducible Wip1 phosphatase mediates a negative feedback regulation of p38 MAPK-p53 signaling in response to UV radiation", The EMBO Journal, vol. 19, pp. 6517-6526.
Tan et al., 2009, "PPM1D is a Potential Therapeutic Target in Ovarian Clear Cell Carcinoma", Clin. Cancer Res., vol. 15, p. 2269-2280.
Vichai et al. 2006, "Sulforhodamine B colorimetric assay for cytotoxicitiy screening", Nature Protocols, vol. 1, No. 3, pp. 1112-1116.
Yoda et al., 2006, "Intrinsic Kinase Activity and SQ/TQ Domain of Chk2 Kinase as Well as N-terminal Domain of Wip1 Phosphatase Are Required for Regulation of Chk2 by Wip1", J. Biol. Chem., vol. 281, pp. 24847 24862.
Yonamine K et al., 1999, "Establishment and characterization of human ovarian clear cell adenocarcinoma cell line (SMOV-2), and its cytotoxicity by anticancer agents", Human Cell, vol. 12, No. 3, pp. 139-148.
Yu et al., 2007, "Overexpression of the wip1 gene abrogates the p38 MAPK/p53/Wip1 pathway and silences p16 expression in human breast cancers", Breast Cancer Res. Treat., vol. 101, pp. 269-278.
International Search Report for PCT/GB2013/052213, dated Oct. 29, 2013. 2 pages.
Aydin et al., "Synthesis, Crystal Structure and Spectroscopic Characterization of (6-[2-(2-chlorophenyl)-1,3-thiazol-4-yl]-2-oxo-1,3-benzothiazol-3(2H)-yl)Acetic Acid" J. Chem. Crystallogr. vol. 40, 2010, pp. 816-820.

* cited by examiner

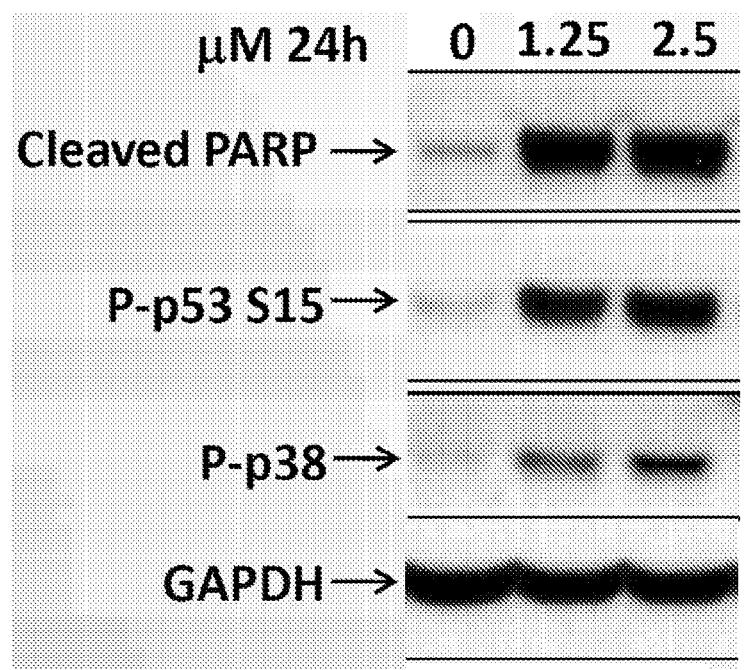

FUSED HETEROCYCLIC COMPOUNDS AND THEIR USE

CROSS-REFERENCE TO RELATED APPLICATIONS

This application is the U.S. national phase entry of PCT/GB2013/052213, with an international filing date of Aug. 22, 2013, which claims priority from U.S. Provisional Application Ser. No. 61/692,321, filed Aug. 23, 2012, the entire contents of which are incorporated herein by reference.

TECHNICAL FIELD

The present invention pertains generally to the field of therapeutic compounds, and more specifically to certain substituted heterocyclic compounds.

The present invention also pertains to pharmaceutical compositions comprising such compounds, to the use of such compounds and compositions, in vitro or in vivo, to kill cells and/or inhibit cell proliferation, to the use of such compounds and compositions to treat proliferative disorders such as cancer, and to methods for their preparation.

BACKGROUND

PPM1D (also known as PP2Cδ, Wip1) is a member of the PP2C class of protein phosphates and is known to have a role in regulating cell growth and cellular stress response.

The expression of PPM1D was initially identified as induced in a p53-dependent manner in response to gamma or UV radiation (1), and PPM1D has been implicated in the negative regulation of tumor suppressor pathways (2).

PPM1D mediates feedback regulation of p38-p53 signaling by inactivation of p38 MAP kinase, MAPK/p38 (1, 3-4) via dephosphorylation, which in turn reduces the phosphorylation and activation of p53.

In addition, PPM1D has been shown to dephosphorylate p53 directly (5). Additional functions for PPM1D include the regulation of the base excision pathway of DNA repair (6), progesterone receptor function (7), the homoeostatic regulation of the checkpoint kinases CHK1 and CHK2 (5, 8-11) and the activation of ataxia-telangiectasia mutated (12).

The PPM1D gene maps to 17q23.2, a genomic region recurrently amplified in several types of tumours including medulloblastomas, neuroblastomas, pancreatic adenocarcinomas, ovarian clear cell carcinomas and breast cancer (4, 13-20).

Studies in the Institute of Cancer Research have demonstrated that PPM1D expression and phosphatase activity are required for the survival of cancer cells derived from breast and ovarian clear cell carcinomas harbouring amplification of 17q23.2 (13, 15). All cases harbouring PPM amplification displayed PPM overexpression. PPM amplification was significantly associated with HER2 overexpression, and HER2, TOP2A and CCND1 amplification (16).

These results provide evidence that PPM1D is one of the drivers of this amplicon and that PPM may constitute a therapeutic target for a subgroup of breast and ovarian cancers harbouring PPM1D gene amplification.

The PPM1D gene has been found to be overexpressed and amplified in many types of cancers, including but not limited to breast cancer, gastric carcinomas, ovarian clear cell adenocarcinoma, pancreatic adenocarcinoma, neuroblastomas, and medulloblastomas. Without wishing to be bound by theory, it is thought that PPM1D amplification or overexpression may also be associated with a particularly poor prognosis in these cancers.

PPM has also been identified as a potential therapeutic target in ovarian clear cell carcinomas (15) and breast cancer (23). In addition, it was recently shown that PPM1D confers CDDP (cis-diammine-dichloroplatinum) resistance in OVCA cells, through attenuating CDDP-induced, Chk1-mediated, p53-dependent apoptosis (21).

Tumours with PPM amplification rarely contain p53 mutations and exhibit poorer prognosis than their counterparts with normal PPM1D.

Diagnostic Markers for PPM Amplification

The availability of molecular diagnostics to identify the group of patients that may benefit from PPM1D inhibitors facilitates the development of biology-driven clinical trials to test PPM as a therapeutic target.

The Institute of Cancer Research has developed reagents that can be used for the identification of PPM1D amplification and overexpression in breast cancer archival samples, including a CISH probe for PPM1D (22).

Given the lack of validated anti-PPM1D antibodies that can be applied for immunohistochemistry, a TaqMan based qRT-PCR which has been validated at ICR may constitute an alternative to assess PPM1D expression levels in routinely processed pathological samples, provided that the samples have an excess of 50% of tumour cells.

REFERENCES

1. Fiscella et al (1997). Wip1, a novel human protein phosphatase that is induced in response to ionizing radiation in a p53-dependent manner. Proc Natl Acad Sci USA 94, 6048-6053.
2. Lammers et al (2007). Role of Type 2C Protein Phosphatases in Growth Regulation and in Cellular Stress Signaling. Crit. Rev. Biochem. Mol. Biol. 42: 437-461.
3. Takekawa et al (2000). p53-inducible Wip1 phosphatase mediates a negative feedback regulation of p38 MAPK-p53 signaling in response to UV radiation. The EMBO Journal 19, 6517-6526.
4. Bulavin D V, Phillips C, Nannenga B, et al (2004). Inactivation of the Wip1 phosphatase inhibits mammary tumorigenesis through p38 MAPK-mediated activation of the p16(Ink4a)-p19(Arf) pathway. Nat Genet 36, 343-350.
5. Lu et al (2005). PPM dephosphorylates Chk1 and p53 and abrogates cell cycle checkpoints. Genes Dev 19, 1162-1174.
6. Lu et al. (2004). The p53-Induced Oncogenic Phosphatase PPM1D Interacts with Uracil DNA Glycosylase and Suppresses Base Excision Repair. Mol Cell 15, 621-634.
7. Proia et al. (2006). Dual Roles for the Phosphatase PPM1D in Regulating Progesterone Receptor Function. J Biol Chem 281, 7089-7101.
8. Fujimoto et al (2006). Regulation of the antioncogenic Chk2 kinase by the oncogenic Wip1 phosphatase. Cell Death Differ. 13, 1170-1180
9. Nannenga et al (2006). Augmented cancer resistance and DNA damage response phenotypes in PPM1D null mice. Mol Carcinog 45: 594-604.
10. Oliva-Trastoy et al (2007). The Wip1 phosphatase (PPM1D) antagonizes activation of the Chk2 tumour suppressor kinase. Oncogene 26: 1449-1458.
11. Yoda et al. (2006). Intrinsic Kinase Activity and SQ/TQ Domain of Chk2 Kinase as Well as N-terminal Domain of Wip1 Phosphatase Are Required for Regulation of Chk2 by Wip1. J Biol Chem 281: 24847-24862.

12. Shreeram et al (2006. Wip1 phosphatase modulates ATM-dependent signaling pathways. Mol Cell. 23(5): 757-64.
13. Natrajan R, Lambros M B, Rodriguez-Pinilla S M, et al (2009). Tiling path genomic profiling of grade 3 invasive ductal breast cancers. Clin Cancer Res 15, 2711-2722.
14. Castellino R C, De Bortoli M, Lu X, Moon S H, Nguyen T A, Shepard M A, Rao P H, Donehower L A, Kim J Y (2008). Medulloblastomas overexpress the p53-inactivating oncogene WIP1/PPM1D. J Neuro-oncol 86, 245-256.
15. Tan D S, Lambros M B, Rayter S, et al (2009) PPM is a potential therapeutic target in ovarian clear cell carcinomas. Clin Cancer Res 15, 2269-2280.
16. Natrajan R, Weigelt B, Mackay A, et al (2009). An integrative genomic and transcriptomic analysis reveals molecular pathways and networks regulated by copy number aberrations in basal-like, HER2 and luminal cancers. Breast Cancer Res Treat 121, 575-589.
17. Bulavin D V, Demidov O N, Saito S, et al (2002). Amplification of PPM1D in human tumors abrogates p53 tumor-suppressor activity. Nat Genet 31, 210-215.
18. Hu X, Stern H M, Ge L, et al (2009). Genetic alterations and oncogenic pathways associated with breast cancer subtypes. Mol Cancer Res 7, 511-522.
19. Loukopoulos P, Shibata T, Katoh H, et al (2007). Genome-wide array-based comparative genomic hybridization analysis of pancreatic adenocarcinoma: identification of genetic indicators that predict patient outcome. Cancer Sci 98, 392-400.
20. Saito-Ohara F, Imoto I, Inoue J, et al (2003). PPM1D is a potential target for 17q gain in neuroblastoma. Cancer Res 63, 1876-1883.
21. Ali A Y, Abedini M R, Tsang B K (2011). The oncogenic phosphatase PPM1D confers cisplatin resistance in ovarian carcinoma cells by attenuating checkpoint kinase 1 and p53 activation. Oncogene. doi: 10.1038/onc.2011.399 [e-publication].
22. Lambros M B, Natrajan R, Geyer F C, Lopez-Garcia M A, Dedes K J, Savage K, Lacroix-Triki M, Lord C J, Linardopoulos S, Ashworth A, Reis-Filho J S (2010). PPM overexpression and gene amplification in breast cancers:qRT-PCR and chromogenic in situ hybridisation study. Modern Pathology 2010 October; 23(10):1334-45.
23. Yu et al (2007). Overexpression of the wip1 gene abrogates the p38 MAPK/p53/Wip1 pathway and silences p16 expression in human breast cancers. Breast Cancer Res. Treat. 101: 269-278.

General Notes

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

SUMMARY OF THE INVENTION

In light of the above discussion, it can be seen that the development of novel compounds and compositions which selectively kill or inhibit the growth of PPM1D-amplified tumour cells would be a contribution to the art.

The present inventors have developed a novel class of substituted heterocyclic compounds with potent and selective cytotoxic activity against PPM1D-amplified cell lines.

Without wishing to be bound by theory, it is thought that the compounds of the invention operate via a novel mechanism which does not involve direct PPM1D inhibition but which nevertheless results in selective activity against PPM1D-amplified cells.

Accordingly, one aspect of the present invention pertains to certain such heterocyclic compounds, as further described herein.

Another aspect of the invention pertains to compositions (e.g., a pharmaceutical compositions) comprising a compound of the invention as described herein and a pharmaceutically acceptable carrier or diluent.

Another aspect of the invention pertains to methods of preparing a composition (e.g., a pharmaceutical composition) comprising the step of admixing a compound of the invention as described herein and a pharmaceutically acceptable carrier or diluent.

Another aspect of the present invention pertains to methods of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a compound of the invention as described herein.

Another aspect of the present invention pertains to methods of treatment comprising administering to a subject in need of treatment a therapeutically-effective amount of a compound of the invention as described herein, preferably in the form of a pharmaceutical composition.

Another aspect of the present invention pertains to a compound of the invention as described herein for use in a method of treatment of the human or animal body by therapy.

Another aspect of the present invention pertains to use of a compound of the invention as described herein, in the manufacture of a medicament for use in treatment.

In some embodiments, the treatment is treatment of a proliferative disorder. In some embodiments, the treatment is treatment of cancer, in particular a cancer characterised by over-expression of PP1MD.

Another aspect of the present invention pertains to a kit comprising (a) a compound of the invention as described herein, preferably provided as a pharmaceutical composition and in a suitable container and/or with suitable packaging; and (b) instructions for use, for example, written instructions on how to administer the compound.

Another aspect of the present invention pertains to certain methods of synthesis, as described herein.

Another aspect of the present invention pertains to a compound (e.g., a compound of the invention) obtainable by a method of synthesis as described herein, or a method comprising a method of synthesis as described herein.

Another aspect of the present invention pertains to a compound (e.g., a compound of the invention) obtained by a method of synthesis as described herein, or by a method comprising a method of synthesis as described herein.

As will be appreciated by one of skill in the art, features and preferred embodiments of one aspect of the invention will also pertain to other aspect of the invention.

BRIEF DESCRIPTION OF THE FIGURES

FIG. 1 provides an image showing the results of a Western Blot (LDS-PAGE gel) for cleaved PARP, Phospho-p53 S15, Phospho-p38, and GAPDG, confirming modulation of the biomarkers expected for PP1 MD-mediated inhibition in SMOV2 cells as described in Example 2.

DETAILED DESCRIPTION OF THE INVENTION

Compounds

One aspect of the present invention pertains to compounds as described in more detail in the numbered paragraphs below and to salts, hydrates, and solvates thereof (e.g., pharmaceutically acceptable salts, hydrates, and solvates thereof).

A compound of general formula I:

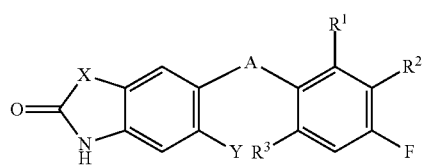

(I)

wherein A is selected from

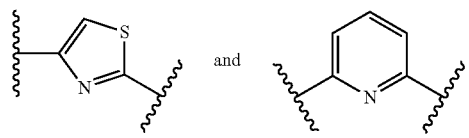 [SMILES: *c1csc(*)n1 ; *c1cccc(*)n1]

and wherein:

X is selected from O, S, $CH_2$, $NR^{N1}$
  wherein
    $R^{N1}$ is selected from H, $C_{1-4}$alkyl, $-L^A-NR^{A1}R^{A2}$, $-L^A-OR^A$,
    where $L^A$ is $C_{1-3}$ alkylene and each $R^A$ is independently selected from H and $C_{1-4}$alkyl;

Y is selected from H, F, and Cl;

$R^1$ is selected from H, F, cyclopropyl, and $CH_2—Z^B$,
  wherein $Z^B$ is selected from:
    H, F, Cl, Me, $—CH=CH_2$, heterocyclyl,
    $—OR^{B1}$, $—NR^{B1}R^{B2}$,
    $-L^{B1}-OR^{B1A}$, $-L^{B1}-NR^{B1A}R^{B1B}$, $-L^{B1}-R^{B1C}$,
    $—O-L^{B2}-OR^{B2A}$, $—O-L^{B2}-NR^{B2A}R^{B2B}$, $—O-L^{B2}-R^{B2C}$,
    $—NH-L^{B2}-OR^{B2A}$, $—NH-L^{B2}-NR^{B2A}R^{B2B}$ and $—NH-L^{B2}-R^{B2C}$ wherein $R^{B1}$ and $R^{B2}$ are each independently H or $C_{1-4}$alkyl,
      $L^{B1}$ is $C_{1-3}$ alkylene, $R^{B1A}$ and $R^{B1B}$ are each independently H or $C_{1-4}$alkyl and $R^{B1C}$ is heterocyclyl,
      and $L^{B2}$ is $C_{1-3}$ alkylene, $R^{B2A}$ and $R^{B2B}$ are each independently H or $C_{1-4}$alkyl and $R^{B2C}$ is heterocyclyl;

$R^2$ is selected from H, F, and Me; and
$R^3$ is selected from H, F and Me.

Variable X

X is selected from O, S, $CH_2$, $NR^{N1}$ wherein $R^{N1}$ is selected from H, $C_{1-4}$alkyl, $L^A-NR^{A1}R^{A2}$, $L^A-OR^{A1}$; where $L^A$ is $C_{1-3}$ alkylene and $R^{A1}$ and $R^{A2}$ are each independently selected from H and $C_{1-4}$alkyl.

A compound according to paragraph [001] wherein X is O.

A compound according to paragraph [001] wherein X is S.

A compound according to paragraph [001] wherein X is $CH_2$.

A compound according to paragraph [001] wherein X is $NR^{N1}$.

A compound according to paragraph [005] wherein $R^{N1}$ is H.

A compound according to paragraph [005] wherein $R^{N1}$ is selected from $C_{1-4}$alkyl, $L^A-NR^{A1}R^{A2}$, and $L^A-OR^A$.

A compound according to paragraph [007] wherein $R^{N1}$ is $C_{1-4}$alkyl.

A compound according to paragraph [008] wherein $R^{N1}$ is selected from Me, Et, nPr, iPr, nBu, sBu, iBu, and tBu.

A compound according to paragraph [009] wherein $R^{N1}$ is Me.

A compound according to paragraph [007] wherein $R^{N1}$ is selected from $L^A-NR^{A1}R^{A2}$, and $L^A-OR^A$.

A compound according to paragraph [011] wherein $R^{N1}$ is $L^A-NR^{A1}R^{A2}$.

A compound according to paragraph [011] wherein $R^{N1}$ is $L^A-OR^A$.

A compound according to any one of paragraphs [011] to [013] wherein $R^{A1}$ is independently selected from H, Me, Et, nPr, iPr, nBu, sBu, iBu, and tBu.

A compound according to any one of paragraphs [011] to [013] wherein $R^{A1}$ is independently H.

A compound according to any one of paragraphs [011] to [013] wherein $R^{A1}$ is independently selected from Me, Et, nPr, iPr, nBu, sBu, iBu, and tBu.

A compound according to any one of paragraphs [011] to [013] wherein $R^{A1}$ is independently Me.

A compound according to any one of paragraphs [011] to [017] wherein $R^{A2}$, if present, is independently selected from H, Me, Et, nPr, iPr, nBu, sBu, iBu, and tBu.

A compound according to any one of paragraphs [011] to [017] wherein $R^{A2}$, if present, is independently H.

A compound according to any one of paragraphs [011] to [017] wherein $R^{A2}$, if present, is independently selected from Me, Et, nPr, iPr, nBu, sBu, iBu, and tBu.

A compound according to any one of paragraphs [011] to [017] wherein $R^{A2}$, if present, is independently Me.

A compound according to paragraph [012] wherein $R^{A1}$ and $R^{A2}$ are both Me.

A compound according to any one of paragraphs [011] to [022] wherein $L^A$ is independently selected from:
—CH$_2$—
—CH$_2$CH$_2$—
—CH$_2$CH(CH$_3$)—
—CH(CH$_3$)CH$_2$—
—CH$_2$CH$_2$CH$_2$—.

A compound according to any one of paragraphs [011] to [022] wherein $L^A$ is independently selected from:
—CH$_2$—
—CH$_2$CH$_2$—
—CH$_2$CH$_2$CH$_2$—.

A compound according to any one of paragraphs [011] to [022] wherein $L^A$ is independently selected from:
—CH$_2$—
—CH$_2$CH$_2$—.

A compound according to any one of paragraphs [011] to [022] wherein $L^A$ is independently —CH$_2$CH$_2$—.

A compound according to paragraph [011] wherein $R^{N1}$ is CH$_2$CH$_2$NMe$_2$.

Variable Y

Y is selected from H, F, and Cl;

A compound according to any one of paragraphs [001] to [027] wherein Y is H.

A compound according to any one of paragraphs [001] to [027] wherein Y is F.

A compound according to any one of paragraphs [001] to [027] wherein Y is Cl.

Group $R^1$ $R^1$ is selected from H, F, cyclopropyl, and CH$_2$—$Z^B$,
  wherein $Z^B$ is selected from:
  H, F, Cl, Me, —CH=CH$_2$, heterocyclyl,
  —OR$^{B1}$, —NR$^{B1}$R$^{B2}$,
  -L$^{B1}$-OR$^{B1A}$, -L$^{B1}$-NR$^{B1A}$R$^{B1B}$, L$^{B1}$-R$^{B1C}$,
  —O-L$^{B2}$-OR$^{B2A}$, —O-L$^{B2}$-NR$^{B2A}$R$^{B2B}$, —O-L$^{B2}$-R$^{B2C}$,
  —NH-L$^{B2}$-OR$^{B2A}$, —NH-L$^{B2}$-NR$^{B2A}$R$^{B2B}$ and —NH-L$^{B2}$-R$^{B2C}$
    wherein $R^{B1}$ and $R^{B2}$ are each independently H or C$_{1-4}$alkyl,
    L is C$_{1-3}$ alkylene, $R^{B1A}$ and $R^{B1B}$ are each independently H or C$_{1-4}$alkyl and $R^{B1C}$ is heterocyclyl,
    and $L^{B2}$ is C$_{1-3}$ alkylene, $R^{B2A}$ and $R^{B2B}$ are each independently H or C$_{1-4}$alkyl and $R^{B2C}$ is heterocyclyl.

A compound according to any one of paragraphs [001] to [030] wherein $R^1$ is H.

A compound according to any one of paragraphs [001] to [030] wherein $R^1$ is F.

A compound according to any one of paragraphs [001] to [030] wherein $R^1$ is cyclopropyl:

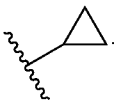 [SMILES: *C1CC1]

A compound according any one of paragraphs [001] to [030] wherein $R^1$ is CH$_2$—$Z^B$.

A compound according to paragraph [034] wherein $Z^B$ is selected from H, F, Cl, Me, —CH=CH$_2$, and heterocyclyl.

A compound according to paragraph [035] wherein $Z^B$ is H (i.e. wherein $R^1$ is Me).

A compound according to paragraph [035] wherein $Z^B$ is Me (i.e. wherein $R^1$ is Et).

A compound according to paragraph [035] wherein $Z^B$ is CH=CH$_2$ (i.e. wherein $R^1$ is allyl).

A compound according to paragraph [035] wherein $Z^B$ is selected from F and Cl.

A compound according to paragraph [039] wherein $Z^B$ is F.

A compound according to paragraph [035] wherein $Z^B$ is heterocyclyl.

A compound according to paragraph [041] wherein $Z^B$ is selected from pyrrolidino piperidino, morpholino, piperizino, and (N—C$_{1-4}$alkyl)-piperizino.

A compound according to paragraph [041] wherein $Z^B$ is selected from pyrrolidino and morpholino.

A compound according to paragraph [041] wherein $Z^B$ is pyrrolidino:

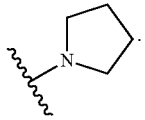 [SMILES: *N1CCCC1]

A compound according to paragraph [041] wherein $Z^B$ is morpholino:

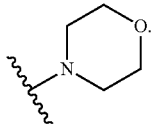 [SMILES: *N1CCOCC1]

A compound according to paragraph [034] wherein $Z^B$ is selected from —OR$^{B1}$ and —NR$^{B1}$R$^{B2}$.

A compound according to paragraph [044] wherein $Z^B$ is —OR$^{B1}$.

A compound according to paragraph [044] wherein $Z^B$ is —NR$^{B1}$R$^{B2}$.

A compound according to any one of paragraphs [044] to [046] wherein $R^{B1}$ is independently selected from H, Me, Et, nPr, iPr, nBu, sBu, iBu, and tBu.

A compound according to any one of paragraphs [044] to [046] wherein $R^{B1}$ is independently H.

A compound according to any one of paragraphs [044] to [046] wherein $R^{B1}$ is independently selected from Me, Et, nPr, iPr, nBu, sBu, iBu, and tBu.

A compound according to any one of paragraphs [044] to [046] wherein $R^{B1}$ is independently Me.

A compound according to any one of paragraphs [044] to [050] wherein $R^{B2}$, if present, is independently selected from H, Me, Et, nPr, iPr, nBu, sBu, iBu, and tBu.

A compound according to any one of paragraphs [044] to [050] wherein $R^{B2}$, if present, is independently H.

A compound according to any one of paragraphs [044] to [050] wherein $R^{B2}$, if present, is independently selected from Me, Et, nPr, iPr, nBu, sBu, iBu, and tBu.

A compound according to any one of paragraphs [044] to [050] wherein $R^{B2}$, if present, is independently Me.

A compound according to paragraph [046] wherein $R^{B1}$ and $R^{B2}$ are both Me.

A compound according to paragraph [034] wherein $Z^B$ is selected from -L$^{B1}$-OR$^{B1A}$, -L$^{B1}$-NR$^{B1A}$R$^{B1B}$, and -L$^{B1}$-R$^{B1C}$.

A compound according to paragraph [056] wherein $Z^B$ is $-L^{B1}-OR^{B1A}$.

A compound according to paragraph [056] wherein $Z^B$ is $-L^{B1}-NR^{B1A}R^{B1B}$.

A compound according to any one of paragraphs [056] to [058] wherein $R^{B1A}$ is independently selected from H, Me, Et, nPr, iPr, nBu, sBu, iBu, and tBu.

A compound according to any one of paragraphs [056] to [058] wherein $R^{B1A}$ is independently H.

A compound according to any one of paragraphs [056] to [058] wherein $R^{B1A}$ is independently selected from Me, Et, nPr, iPr, nBu, sBu, iBu, and tBu.

A compound according to any one of paragraphs [056] to [058] wherein $R^{B1A}$ is independently Me.

A compound according to any one of paragraphs [056] to [062] wherein $R^{B1B}$, if present, is independently selected from H, Me, Et, nPr, iPr, nBu, sBu, iBu, and tBu.

A compound according to any one of paragraphs [056] to [062] wherein $R^{B1B}$, if present, is independently H.

A compound according to any one of paragraphs [056] to [062] wherein $R^{B1B}$, if present, is independently selected from Me, Et, nPr, iPr, nBu, sBu, iBu, and tBu.

A compound according to any one of paragraphs [056] to [062] wherein $R^{B1B}$, if present, is independently Me.

A compound according to paragraph [058] wherein $R^{B1A}$ and $R^{B1B}$ are both Me.

A compound according to paragraph [056] wherein $Z^B$ is $-L^{B1}-R^{B1C}$.

A compound according to paragraph [068] wherein $R^{B1C}$ is a heterocyclyl group selected from pyrrolidino piperidino, morpholino, piperizino, and (N—$C_{1-4}$alkyl)-piperizino.

A compound according to paragraph [069] wherein $R^{B1C}$ is selected from pyrrolidino and morpholino.

A compound according to paragraph [069] wherein $R^{B1C}$ is pyrrolidino.

A compound according to paragraph [069] wherein $R^{B1C}$ is morpholino.

A compound according to any one of paragraphs [056] to [072] wherein $L^{B1}$ is independently selected from:
—$CH_2$—
—$CH_2CH_2$—
—$CH_2CH(CH_3)$—
—$CH(CH_3)CH_2$—
—$CH_2CH_2CH_2$—.

A compound according to any one of paragraphs [056] to [072] wherein $L^{B1}$ is independently —$CH_2$—.

A compound according to paragraph [034] wherein $Z^B$ is selected from —O-$L^{B2}$-$OR^{B2A}$, —O-$L^{B2}$-$NR^{B2A}R^{B2B}$, —O-$L^{B2}$-$R^{B2C}$, —NH-$L^{B2}$-$OR^{B2A}$, —NH-$L^{B2}$-$NR^{B2A}R^{B2B}$ and —NH-$L^{B2}$-$R^{B2C}$.

A compound according to paragraph [075] wherein $Z^B$ is selected from —O-$L^{B2}$-$R^{B2A}$ and —NH-$L^{B2}$-$OR^{B2A}$.

A compound according to paragraph [075] wherein $Z^B$ is —O-$L^{B2}$-$OR^{B2A}$.

A compound according to paragraph [075] wherein $Z^B$ is —NH-$L^{B2}$-$OR^{B2A}$.

A compound according to paragraph [075] wherein $Z^B$ is selected from —O-$L^{B2}$-$NR^{B2A}R^{B2B}$ and —NH-$L^{B2}$-$NR^{B2A}R^{B2B}$.

A compound according to paragraph [075] wherein $Z^B$ is —O-$L^{B2}$-$NR^{B2A}R^{B2B}$.

A compound according to paragraph [075] wherein $Z^B$ is —NH-$L^{B2}$-$NR^{B2A}R^{B2B}$.

A compound according to any one of claims [075] to [081] wherein $R^{B2A}$ is independently selected from H, Me, Et, nPr, iPr, nBu, sBu, iBu, and tBu.

A compound according to any one of paragraphs [075] to [081] wherein $R^{B2A}$ is independently H.

A compound according to any one of paragraphs [075] to [081] wherein $R^{B2A}$ is independently selected from Me, Et, nPr, iPr, nBu, sBu, iBu, and tBu.

A compound according to any one of paragraphs [075] to [081] wherein $R^{B2A}$ is independently Me.

A compound according to any one of paragraphs [075] to [085] wherein $R^{B2B}$, if present, is independently selected from H, Me, Et, nPr, iPr, nBu, sBu, iBu, and tBu.

A compound according to any one of paragraphs [075] to [085] wherein $R^{B2B}$, if present, is independently H.

A compound according to any one of paragraphs [075] to [085] wherein $R^{B2B}$, if present, is independently selected from Me, Et, nPr, iPr, nBu, sBu, iBu, and tBu.

A compound according to any one of paragraphs [075] to [085] wherein $R^{B2B}$, if present, is independently Me.

A compound according to any one of paragraphs [079] to [081] wherein $R^{B2A}$ and $R^{B2B}$ are both Me.

A compound according to paragraph [075] wherein $Z^B$ is selected from —O-$L^{B2}$-$R^{B2C}$ and —NH-$L^{B2}$-$R^{B2C}$.

A compound according to paragraph [075] wherein $Z^B$ is —O-$L^{B2}$-$R^{B2C}$.

A compound according to paragraph [075] wherein $Z^B$ is —NH-$L^{B2}$-$R^{B2C}$.

A compound according to any one of paragraphs [091] to [093] wherein $R^{B2C}$ is a heterocyclyl group selected from pyrrolidino piperidino, morpholino, piperizino, and (N—$C_{1-4}$alkyl)-piperizino.

A compound according to paragraph [094] wherein $R^{B2C}$ is selected from pyrrolidino and morpholino.

A compound according to paragraph [094] wherein $R^{B2C}$ is pyrrolidino.

A compound according to paragraph [094] wherein $R^{B2C}$ is morpholino.

A compound according to any one of paragraphs [075] to [097] wherein $L^{B2}$ is independently selected from:
—$CH_2$—
—$CH_2CH_2$—
—$CH_2CH(CH_3)$—
—$CH(CH_3)CH_2$—
—$CH_2CH_2CH_2$—.

A compound according to any one of paragraphs [075] to [097] wherein $L^{B2}$ is independently —$CH_2CH_2$— or —$CH_2$—.

A compound according to any one of paragraphs [075] to [097] wherein $L^{B2}$ is independently —$CH_2CH_2$.

Group $R^2$ $R^2$ is selected from H, F, and Me.

A compound according to any one of paragraphs [001] to [100] wherein $R^2$ is H.

A compound according to any one of paragraphs [001] to [100] wherein $R^2$ is F.

A compound according to any one of paragraphs [001] to [100] wherein $R^2$ is Me.

Group $R^3$ $R^3$ is selected from H, F and Me

A compound according to any one of paragraphs [001] to [103] wherein $R^3$ is H.

A compound according to any one of paragraphs [001] to [103] wherein $R^3$ is F.

A compound according to any one of paragraphs [001] to [103] wherein $R^3$ is Me.

Certain Preferred Embodiments

In some embodiments, the compound is a compound of formula Ia:

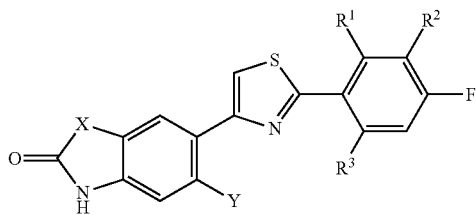 Ia

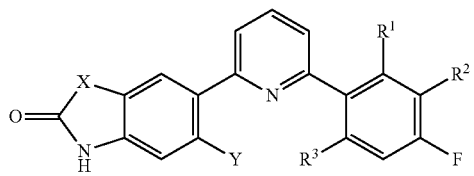 Ib wherein X, Y, $R^1$, $R^2$ and $R^3$ are as previously defined.

In some embodiments, the compound is a compound of formula Ib:

wherein X, Y, $R^1$, $R^2$ and $R^3$ are as previously defined.

In some embodiments, the compound is a compound selected from the following compounds or pharmaceutically acceptable salts thereof:

| Compound Ref | Structure | IUPAC Name |
|---|---|---|
| 1 | 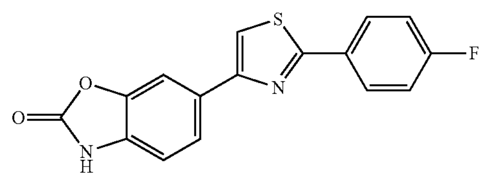 [SMILES: O=c1[nH]c2ccc(-c3csc(-c4ccc(F)cc4)n3)cc2o1] | 6-(2-(4-fluorophenyl)thiazol-4-yl)benzo[d]oxazol-2(3H)-one |
| 2 | 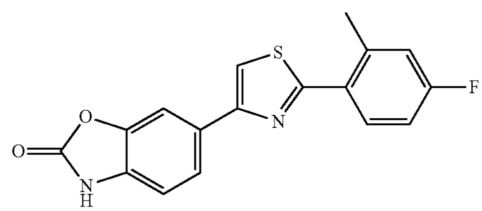 [SMILES: Cc1cc(F)ccc1-c1nc(-c2ccc3[nH]c(=O)oc3c2)cs1] | 6-(2-(4-fluoro-2-methylphenyl)thiazol-4-yl)benzo[d]oxazol-2(3H)-one |
| 3 | 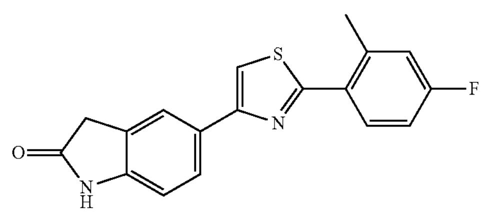 [SMILES: Cc1cc(F)ccc1-c1nc(-c2ccc3c(c2)CC(=O)N3)cs1] | 5-(2-(4-fluoro-2-methylphenyl)thiazol-4-yl)indolin-2-one |
| 4 | 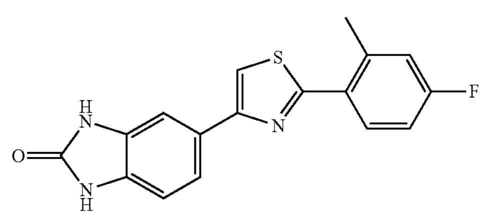 [SMILES: Cc1cc(F)ccc1-c1nc(-c2ccc3[nH]c(=O)[nH]c3c2)cs1] | 5-(2-(4-fluoro-2-methylphenyl)thiazol-4-yl)-1H-benzo[d]imidazol-2(3H)-one |
| 5 | 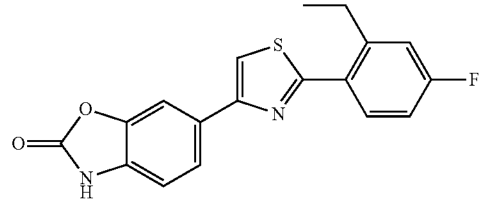 [SMILES: CCc1cc(F)ccc1-c1nc(-c2ccc3[nH]c(=O)oc3c2)cs1] | 6-(2-(2-ethyl-4-fluorophenyl)thiazol-4-yl)benzo[d]oxazol-2(3H)-one |

-continued

| Compound Ref | Structure | IUPAC Name |
|---|---|---|
| 6 | 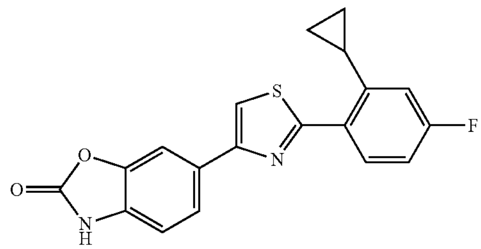 [SMILES: O=c1[nH]c2ccc(-c3csc(-c4ccc(F)cc4C4CC4)n3)cc2o1] | 6-(2-(2-cyclopropyl-4-fluorophenyl)thiazol-4-yl)benzo[d]oxazol-2(3H)-one |
| 7 | 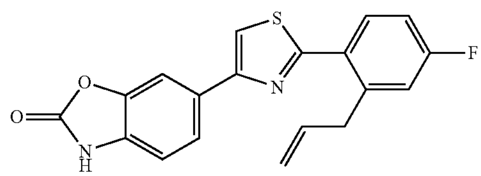 [SMILES: C=CCc1cc(F)ccc1-c1nc(-c2ccc3[nH]c(=O)oc3c2)cs1] | 6-(2-(2-allyl-4-fluorophenyl)thiazol-4-yl)benzo[d]oxazol-2(3H)-one |
| 8 | 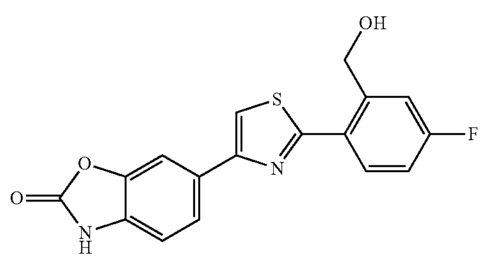 [SMILES: O=c1[nH]c2ccc(-c3csc(-c4ccc(F)cc4CO)n3)cc2o1] | 6-(2-(4-fluoro-2-(hydroxymethyl)phenyl)thiazol-4-yl)benzo[d]oxazol-2(3H)-one |
| 9 | 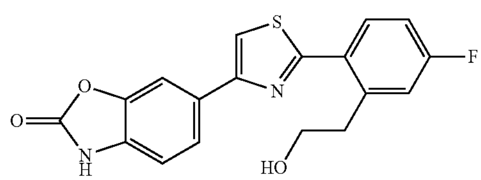 [SMILES: O=c1[nH]c2ccc(-c3csc(-c4ccc(F)cc4CCO)n3)cc2o1] | 6-(2-(4-fluoro-2-(2-hydroxyethyl)phenyl)thiazol-4-yl)benzo[d]oxazol-2(3H)-one |
| 10 | 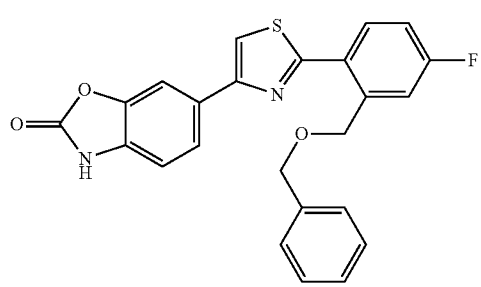 [SMILES: O=c1[nH]c2ccc(-c3csc(-c4ccc(F)cc4COCc4ccccc4)n3)cc2o1] | 6-(2-(2-((benzyloxy)methyl)-4-fluorophenyl)thiazol-4-yl)benzo[d]oxazol-2(3H)-one |
| 11 | 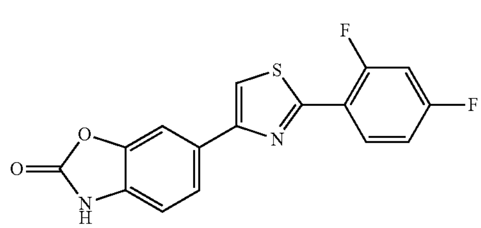 [SMILES: O=c1[nH]c2ccc(-c3csc(-c4ccc(F)cc4F)n3)cc2o1] | 6-(2-(2,4-difluorophenyl)thiazol-4-yl)benzo[d]oxazol-2(3H)-one |

-continued

| Compound Ref | Structure | IUPAC Name |
|---|---|---|
| 12 | 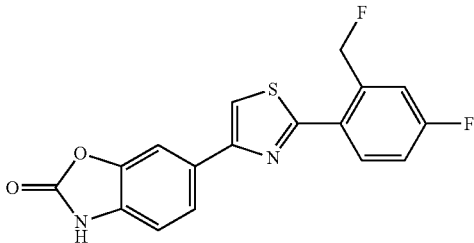 [SMILES: O=c1[nH]c2ccc(-c3csc(-c4ccc(F)cc4CF)n3)cc2o1] | 6-(2-(4-fluoro-2-(fluoromethyl)phenyl)thiazol-4-yl)benzo[d]oxazol-2(3H)-one |
| 13 | 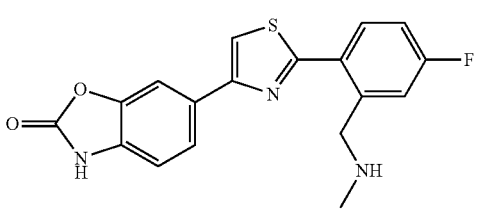 [SMILES: CNCc1cc(F)ccc1-c1nc(-c2ccc3[nH]c(=O)oc3c2)cs1] | 6-(2-(4-fluoro-2-((methylamino)methyl)phenyl)thiazol-4-yl)benzo[d]oxazol-2(3H)-one |
| 14 | 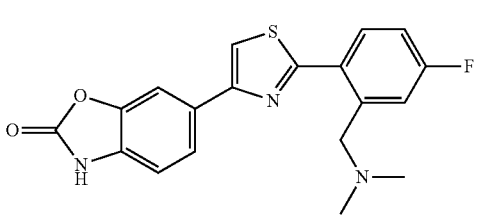 [SMILES: CN(C)Cc1cc(F)ccc1-c1nc(-c2ccc3[nH]c(=O)oc3c2)cs1] | 6-(2-(2-((dimethylamino)methyl)-4-fluorophenyl)thiazol-4-yl)benzo[d]oxazol-2(3H)-one |
| 15 | 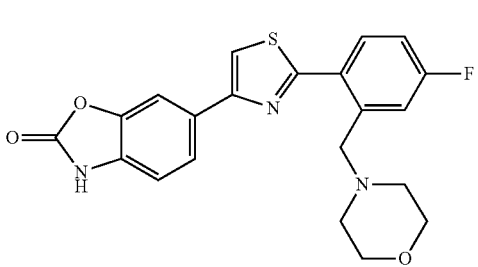 [SMILES: O=c1[nH]c2ccc(-c3csc(-c4ccc(F)cc4CN4CCOCC4)n3)cc2o1] | 6-(2-(4-fluoro-2-(morpholinomethyl)phenyl)thiazol-4-yl)benzo[d]oxazol-2(3H)-one |
| 16 | 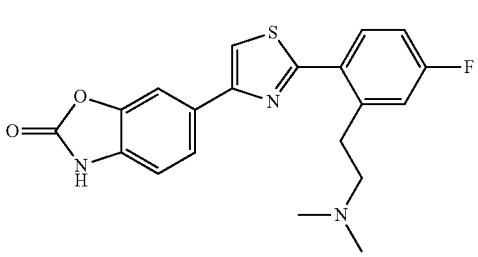 [SMILES: CN(C)CCc1cc(F)ccc1-c1nc(-c2ccc3[nH]c(=O)oc3c2)cs1] | 6-(2-(2-(2-(dimethylamino)ethyl)-4-fluorophenyl)thiazol-4-yl)benzo[d]oxazol-2(3H)-one |
| 17 | 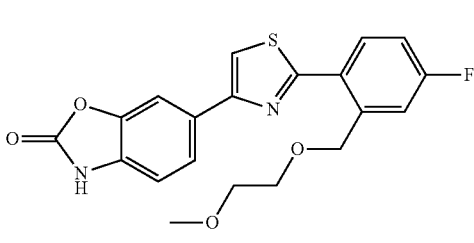 | 6-(2-(4-fluoro-2-((2-methoxyethoxy)methyl)phenyl)thiazol-4-yl)benzo[d]oxazol-2(3H)-one |

-continued

| Compound Ref | Structure | IUPAC Name |
|---|---|---|
| 18 | 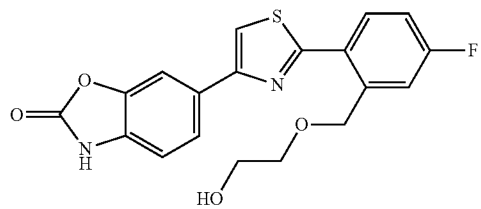 [SMILES: O=c1[nH]c2ccc(-c3csc(-c4ccc(F)cc4COCCO)n3)cc2o1] | 6-(2-(4-fluoro-2-((2-hydroxyethoxy)methyl)phenyl)thiazol-4-yl)benzo[d]oxazol-2(3H)-one |
| 19 | 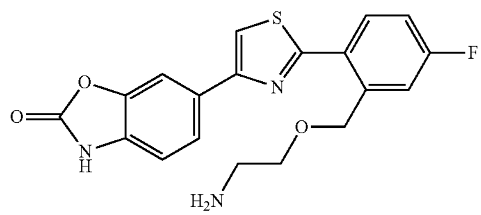 [SMILES: NCCOCc1cc(F)ccc1-c1nc(-c2ccc3[nH]c(=O)oc3c2)cs1] | 6-(2-(2-((2-aminoethoxy)methyl)-4-fluorophenyl)thiazol-4-yl)benzo[d]oxazol-2(3H)-one |
| 20 | 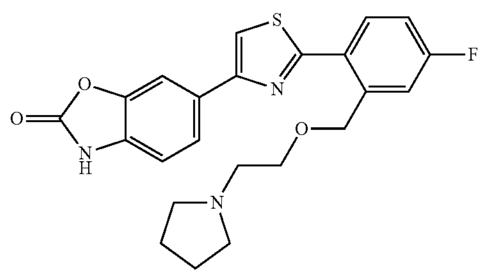 [SMILES: O=c1[nH]c2ccc(-c3csc(-c4ccc(F)cc4COCCN4CCCC4)n3)cc2o1] | 6-(2-(4-fluoro-2-((2-(pyrrolidin-1-yl)ethoxy)methyl)phenyl)thiazol-4-yl)benzo[d]oxazol-2(3H)-one |
| 21 | 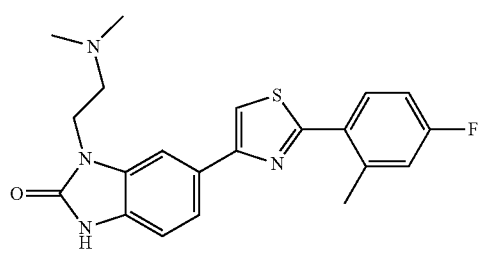 [SMILES: Cc1cc(F)ccc1-c1nc(-c2ccc3[nH]c(=O)n(CCN(C)C)c3c2)cs1] | 1-(2-(dimethylamino)ethyl)-6-(2-(4-fluoro-2-methylphenyl)thiazol-4-yl)-1H-benzo[d]imidazol-2(3H)-one |
| 22 | 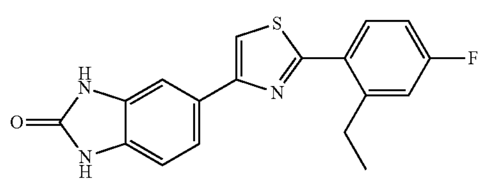 [SMILES: CCc1cc(F)ccc1-c1nc(-c2ccc3[nH]c(=O)[nH]c3c2)cs1] | 5-(2-(2-ethyl-4-fluorophenyl)thiazol-4-yl)-1H-benzo[d]imidazol-2(3H)-one |
| 23 | 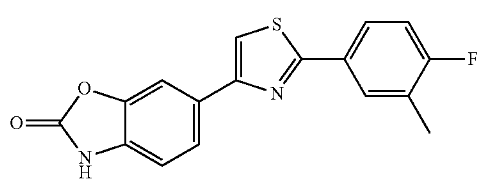 [SMILES: Cc1cc(-c2nc(-c3ccc4[nH]c(=O)oc4c3)cs2)ccc1F] | 6-(2-(4-fluoro-3-methylphenyl)thiazol-4-yl)benzo[d]oxazol-2(3H)-one |
| 24 | 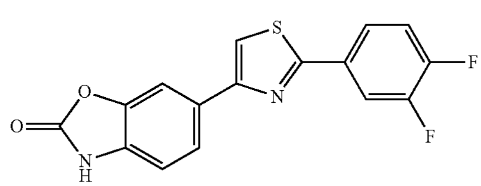 [SMILES: O=c1[nH]c2ccc(-c3csc(-c4ccc(F)c(F)c4)n3)cc2o1] | 6-(2-(3,4-difluorophenyl)thiazol-4-yl)benzo[d]oxazol-2(3H)-one |

-continued

| Compound Ref | Structure | IUPAC Name |
|---|---|---|
| 25 | 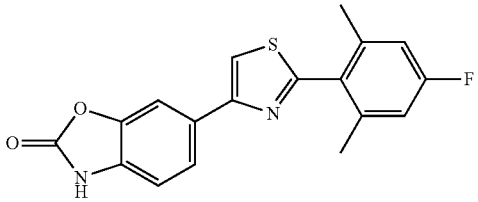 [SMILES: Cc1cc(F)cc(C)c1-c1nc(-c2ccc3[nH]c(=O)oc3c2)cs1] | 6-(2-(4-fluoro-2,6-dimethylphenyl)thiazol-4-yl)benzo[d]oxazol-2(3H)-one |
| 26 | 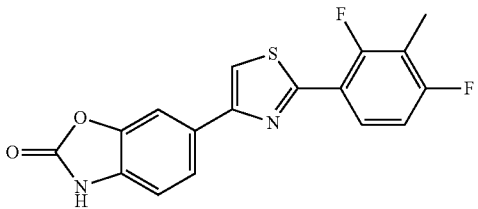 [SMILES: Cc1c(F)ccc(-c2nc(-c3ccc4[nH]c(=O)oc4c3)cs2)c1F] | 6-(2-(2,4-difluoro-3-methylphenyl)thiazol-4-yl)benzo[d]oxazol-2(3H)-one |
| 27 | 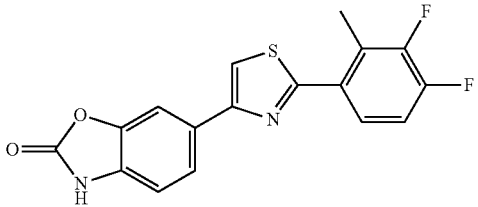 [SMILES: Cc1c(-c2nc(-c3ccc4[nH]c(=O)oc4c3)cs2)ccc(F)c1F] | 6-(2-(3,4-difluoro-2-methylphenyl)thiazol-4-yl)benzo[d]oxazol-2(3H)-one |
| 28 | 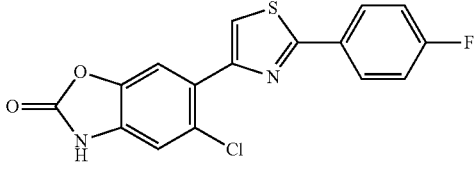 [SMILES: O=c1[nH]c2cc(Cl)c(-c3csc(-c4ccc(F)cc4)n3)cc2o1] | 6-chloro-5-(2-(4-fluorophenyl)thiazol-4-yl)indolin-2-one |
| 29 | 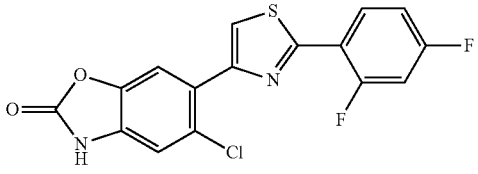 [SMILES: O=c1[nH]c2cc(Cl)c(-c3csc(-c4ccc(F)cc4F)n3)cc2o1] | 6-chloro-5-(2-(2,4-difluorophenyl)thiazol-4-yl)indolin-2-one |
| 30 | 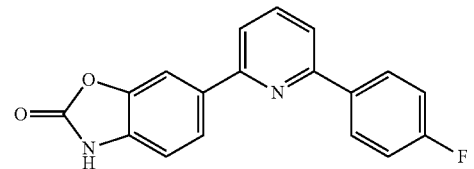 [SMILES: O=c1[nH]c2ccc(-c3cccc(-c4ccc(F)cc4)n3)cc2o1] | 6-(6-(4-fluorophenyl)pyridin-2-yl)benzo[d]oxazol-2(3H)-one |
| 31 | 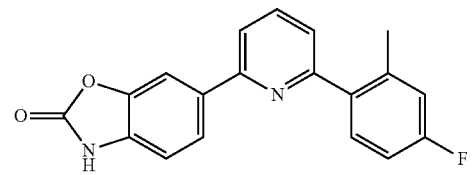 [SMILES: Cc1cc(F)ccc1-c1cccc(-c2ccc3[nH]c(=O)oc3c2)n1] | 6-(6-(4-fluoro-2-methylphenyl)pyridin-2-yl)benzo[d]oxazol-2(3H)-one |

| Compound Ref | Structure | IUPAC Name |
|---|---|---|
| 32 | 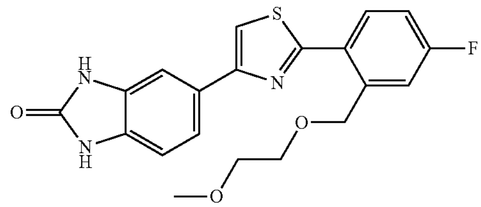 [SMILES: COCCOCc1cc(F)ccc1-c1nc(-c2ccc3[nH]c(=O)[nH]c3c2)cs1] | 5-(2-(4-fluoro-2-((2-methoxyethoxy)methyl)phenyl)thiazol-4-yl)-1H-benzo[d]imidazol-2(3H)-one |

Molecular Weight

In some embodiments the compound has a molecular weight of from 300 to 1000.

In some embodiments the bottom of range is from 300, 310, 320, 330, 340, 350, 375, or 400.

In some embodiments, the top of range is 1000, 900, 700, 600, 550 or 500.

In some embodiments, the range is 340 to 550.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

All combinations of the embodiments pertaining to the chemical groups represented by the variables (e.g., X, Y, $R^1$, $R^2$, $R^3$ etc) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to compounds as described herein, in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In some embodiments, the compound is in a substantially purified form with an optical purity of at least 60% (i.e., 60% of the compound, on a molar basis, is the desired enantiomer, and 40% is the undesired enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

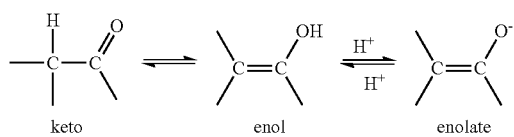

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding hydrate or solvate of the compound (e.g., pharmaceutically acceptable hydrates or solvates of the compound). The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes hydrate and solvate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(═O)CH$_3$, —OAc).

For example, an aldehyde or ketone group may be protected as an acetal (R—CH(OR)$_2$) or ketal (R$_2$C(OR)$_2$), respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O●).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH₂NHC(=O)CH₃).

For example, a carbonyl group may be protected as an oxime (—C(=NOH)—) or a substituted oxime (—C(=NOR)—), for example, where R is saturated aliphatic $C_{1-4}$alkyl.

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Methods for the chemical synthesis of the compounds of the present invention are described herein. These and/or other well-known methods may be modified and/or adapted in known ways in order to facilitate the synthesis of additional compounds within the scope of the present invention.

In one approach, a compound of formula Ia may be prepared by condensing a compound of formula IIa:

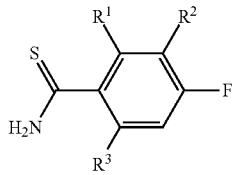

IIa with a compound of formula IIIa:

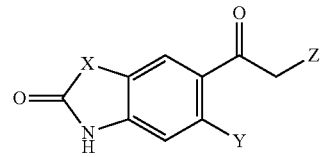

IIIa wherein Z is a halogen, under conditions suitable to form a thiazole ring.

Suitable reaction conditions for thiazole formation are known in the art see, for example, (Kamisuki, S.; Shirakawa, T.; Kugimiya, A.; Abu-Elheiga, L.; Park Choo, H-Y; Yamada, K.; Shimogawa, H.; Wakil, S. J.; Uesugi, M. *J. Med. Chem.* 2011, 54, 4923). In some embodiments, the compounds of formulae IIa and IIIa are heated in a solvent, preferably a polar solvent such as ethanol, in the presence of a quaternary ammonium salt (e.g. tetrabutylammonium bromide).

The thioamide compound of formulae IIa may be synthesised, for example, from the corresponding nitrile compound, of formula IVa:

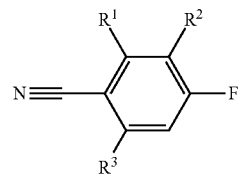

IVa by known methods, for example by treatment with e.g. sodium hydrogen sulfide. Other methods are also known (see, for example, Boys, M.; Downs, V. *Synth. Comm.* 2006, 36, 295; 2) Manaka, A.; Sato, M. *Synth. Comm.* 2005, 35, 761). Suitable nitriles are commercially available or may conveniently be prepared from commercially available starting materials.

The compound of formula IIIa may also be commercially available or conveniently prepared by methods known in the art.

In another approach, a compound of formula Ib may be prepared by coupling a boronic acid compound, for example of formula IIb:

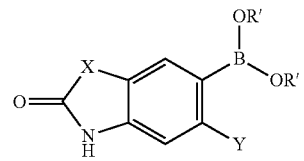

IIa (wherein each R' is hydrogen or alkyl, or where both R,' together with the oxygen to which they are attached, form a 5-membered ring) with a compound of formula IIIb:

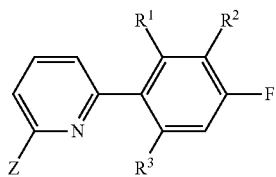

IIIb wherein Z is a halogen, for example in the presence of a Pd(0) catalyst.

In some embodiments, the compound of formula IIb is a compound of formula:

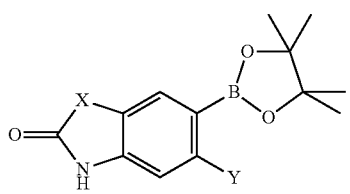

Compounds of formula IIIb may be synthesised by methods known in the art (see, for example, Miyashita, K.; Sakai, T.; Imanishi, T. *Org. Lett.* 2003, 5, 2683) or may be commercially available.

Compounds of formula IIb may be synthesised from the corresponding halo compound, such as a compound of formula IVb:

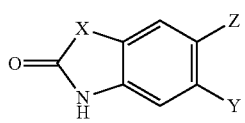

wherein Z is a halogen.

Compositions

One aspect of the present invention pertains to a composition (e.g., a pharmaceutical composition) comprising a compound of the invention, as described herein, and a pharmaceutically acceptable carrier, diluent, or excipient.

Another aspect of the present invention pertains to a method of preparing a composition (e.g., a pharmaceutical composition) comprising admixing a compound of the invention, as described herein, and a pharmaceutically acceptable carrier, diluent, or excipient.

Uses

The compounds of the invention described herein are useful, for example, in the treatment of proliferative disorders, such as, for example, cancer, etc.

Use in Methods of Inhibiting Cell Proliferation, Etc.

The compounds of the invention described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a compound of the invention, as described herein.

In one embodiment, the method is a method of regulating (e.g., inhibiting) cell proliferation (e.g., proliferation of a cell), in vitro or in vivo, comprising contacting a cell with an effective amount of a compound of the invention, as described herein.

In one embodiment, the method is performed in vitro.

In one embodiment, the method is performed in vivo.

In one embodiment, the compound of the invention is provided in the form of a pharmaceutically acceptable composition.

Any type of cell may be treated, including but not limited to, cancer cells derived from tumours or the lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a compound of the invention, as described herein, for use in a method of treatment of the human or animal body by therapy.

Use in the Manufacture of Medicaments

Another aspect of the present invention pertains to use of a compound of the invention, as described herein, in the manufacture of a medicament for use in treatment.

In one embodiment, the medicament comprises the compound.

Methods of Treatment

Another aspect of the present invention pertains to a method of treatment comprising administering to a patient in need of treatment a therapeutically effective amount of a compound of the invention, as described herein, preferably in the form of a pharmaceutical composition.

Conditions Treated—Proliferative Disorders and Cancer

In some embodiments (e.g., of use in methods of therapy, of use in the manufacture of medicaments, of methods of treatment), the treatment is treatment of a proliferative disorder.

The term "proliferative condition," as used herein, pertains to an unwanted or uncontrolled cellular proliferation of excessive or abnormal cells which is undesired, such as, neoplastic or hyperplastic growth.

In some embodiments, the treatment is treatment of: a proliferative condition characterised by benign, pre-malignant, or malignant cellular proliferation, including but not limited to tumours and cancers (see below).

In some embodiments, the treatment is treatment of cancer.

In some embodiments, the cancer is characterised by over-expression of PPM or by amplification of PPM1D. Various cancers with PPM amplification are known in the art, as discussed in the background section above.

Examples of cancers to be treated include, but are not limited to breast cancer, gastric cancer including gastric carcinomas, ovarian cancer, such as ovarian clear cell adenocarcinoma, pancreatic carcinoma, neuroblastomas and medulloblastomas.

In some embodiments, the cancer is selected from breast cancer and ovarian cancer.

In some embodiments, the cancer is selected from breast cancers, such as ERBB2+ breast cancer. In some embodiments, the cancer is selected from breast tumours with PPM amplification, such as ERBB2+ breast cancer with PPM amplification.

In some embodiments, the cancer is selected from ovarian cancer, such as ovarian clear cell carcinoma. In some embodiments, the cancer is an ovarian cancer with PPM amplification.

An anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, molecularly-targeted agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound of the invention as described herein with one or more other (e.g., 1, 2, 3, 4) agents or therapies that regulates cell growth or survival or differentiation via a different mechanism, thus treating several characteristic features of cancer development.

One aspect of the present invention pertains to a compound of the invention as described herein, in combination with one or more additional therapeutic agents, as described below. The particular combination would be at the discretion of the physician who would select dosages using his common general knowledge and dosing regimens known to a skilled practitioner.

The agents (i.e., the compound of the invention described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound of the invention described here, plus one or more other agents) may be formulated together in a single dosage form, or alternatively, the individual agents may be formulated separately and presented together in the form of a kit, optionally with instructions for their use.

Other Uses

The compounds of the invention described herein may also be used as cell culture additives to inhibit cell proliferation, etc.

The compounds of the invention described herein may also be used as part of an in vitro assay, for example, in order to determine whether a candidate host is likely to benefit from treatment with the compound in question.

The compounds of the invention described herein may also be used as a standard, for example, in an assay, in order to identify other compounds, other anti-proliferative agents, other anti-cancer agents, etc.

Kits

One aspect of the invention pertains to a kit comprising (a) a compound of the invention as described herein, or a composition comprising a compound of the invention as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The compound of the invention or pharmaceutical composition comprising the compound of the invention may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a monotreme (e.g. a platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the compound of the invention to be administered alone, it is preferable to present it as a pharmaceutical formulation (e.g., composition, preparation, medicament) comprising at least one compound of the invention, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one compound of the invention, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and *acacia* or tragacanth. Pastilles typically comprise the compound in an inert matrix, such as gelatin and glycerin, or sucrose and *acacia*. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, *acacia*, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the compounds of the invention, and compositions comprising the compounds of the invention, can vary from patient to patient. Determining the optimal dosage will generally involve the balancing of the level of therapeutic benefit against any risk or deleterious side effects. The selected dosage level will depend on a variety of factors including, but not limited to, the activity of the particular compound of the invention, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the compound of the invention is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Synthetic Examples

Synthesis 1

Thiazole-Containing Compounds

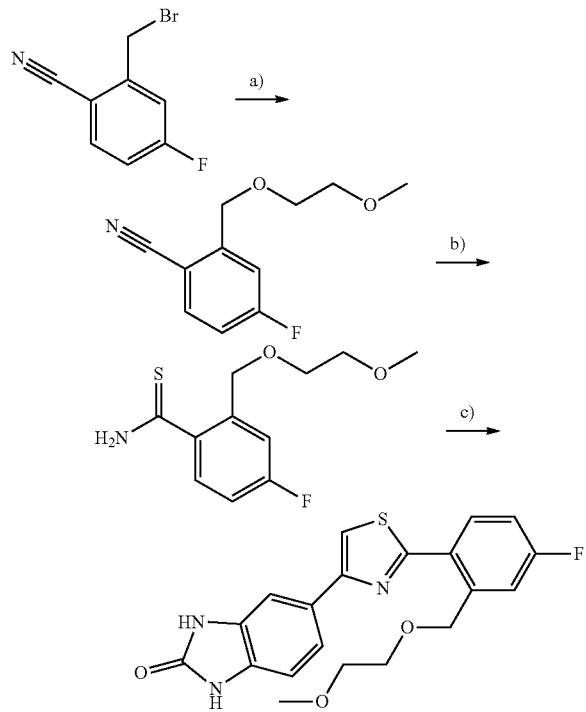

a) 2-methoxyethanol, NaH, THF, −60° C. to RT, 84%; b) NaSH.xH2O, MgCl₂.6H₂O, DMF, RT, 81%; c) 5-(2-chloroacetyl)-1H-benzo[d]imidazol-2(3H)-one, tetrabutylammonium bromide, EtOH, 85° C., 50%.

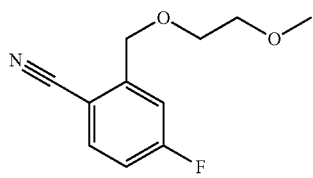

4-fluoro-2((2-methoxyethoxy)methyl)benzonitrile

To a solution of 2-methoxyethanol (953 mg, 12.5 mmol) in THF (60 ml) at −60° C., was added sodium hydride 60% (275 mg, 6.88 mmol) by portion. The solution was stirred at this temperature for 10 min then the cold bath was removed and the reaction was stirred for a further 20 min at room temperature. After this time, the cold bath was put back in place and the reaction was cooled back. When the solution reaches −60° C., 2-(bromomethyl)-4-fluorobenzonitrile (1.337 g, 6.25 mmol) was added to the reaction mixture. The bath was removed 1 h30 later and the reaction was left at room temperature for a further 2 h before being quenched with NH₄Cl sat. (100 ml). The product was extracted with ethyl acetate (3×100 ml) then dried (MgSO₄), and concentrated to dryness. Purification on silica gel with the Biotage SP1 purification system gave the title compound (1.093 g, 84%) as a white solid. ¹H NMR (500 MHz, CDCl₃) δ 7.66 (dd, J=8.5, 5.3 Hz, 1H), 7.39 (dd, J=9.2, 2.6 Hz, 1H), 7.08 (ddd, J=8.2, 8.2, 2.6 Hz, 1H), 4.77 (s, 2H), 3.77-3.76 (m, 2H),), 3.65-3.63 (m, 2H), 3.43 (s, 3H); HRMS m/z 210.0925 for C₁₁H₁₃FNO₂ found 210.0926 (Δ0.42 ppm).

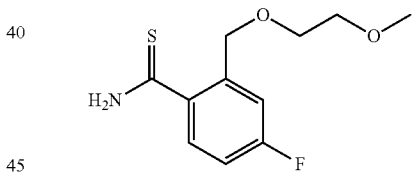

4-fluoro-2-((2-methoxyethoxy)methyl)benzothioamide

To a solution of 4-fluoro-2-((2-methoxyethoxy)methyl) benzonitrile (1.073 g, 5.13 mmol) in DMF (50 ml), was added magnesium chloride hexahydrate (1.563 g, 7.7 mmol) and sodium hydrosulfite (431 mg, 7.7 mmol). The solution was stirred at room temperature for 18 h then the DMF was removed under reduced pressure. Water (100 ml) was added to the residue and the product was extracted with ethyl acetate (3×100 ml). then dried (MgSO₄), and concentrated to dryness. Purification on silica gel with the Biotage SP1 purification system gave the title compound (1.007 g, 81%) as a pale yellow solid. ¹H NMR (500 MHz, CDCl₃) δ 8.92 (br s, 1H), 8.07 (dd, J=8.7, 5.8 Hz, 1H), 7.92 (br s, 1H), 7.10 (ddd, J=8.2, 8.1, 2.7 Hz, 1H), 7.02 (dd, J=8.8, 2.7 Hz, 1H), 4.52 (s, 2H), 3.73-3.71 (m, 2H),), 3.55-3.53 (m, 2H), 3.35 (s, 3H); HRMS m/z 244.0802 for C₁₁H₁₅FNO₂S found 244.0807 (Δ2.18 ppm).

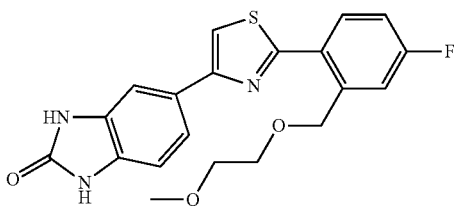 [SMILES: COCCOCc1cc(F)ccc1-c1nc(-c2ccc3[nH]c(=O)[nH]c3c2)cs1]

5-(2-(4-fluoro-2-(2-methoxyethoxy)phenyl)thiazol-4-yl)-1H-benzo[d]imidazol-2(3H)-one 32

To a solution of 4-fluoro-2-((2-methoxyethoxy)methyl) benzothioamide (1.000 g, 4.11 mmol) in ethanol (20 ml), was added 5-(2-chloroacetyl)-1H-benzo[d]imidazol-2(3H)-one (788 mg, 3.74 mmol) and tetrabutylammonium bromide (1.321 g, 4.11 mmol). The solution was then stirred at reflux for 18 h. Upon cooling, silica was added to the reaction mixture and the ethanol was removed under reduced pressure. Purification on silica gel with the Biotage SP1 purification system gave a solid that was recrystallised from ethanol to give the title compound (720 mg, 50%) as an off white solid. $^1$H NMR (500 MHz, DMSO) δ 10.17 (d, J=12.3 Hz, 1H), 8.07 (s, 1H), 7.88 (dd, J=8.6, 5.6 Hz, 1H), 7.64 (dd, J=8.1, 1.6 Hz, 1H), 7.56 (d, J=1.4 Hz, 1H), 7.49 (dd, J=10.3, 2.8 Hz, 1H), 7.30 (ddd, J=8.4, 8.3, 2.9 Hz, 1H), 7.00 (d, J=8.1 Hz, 1H), 4.97 (s, 2H), 3.66-3.64 (m, 2H),), 3.52-3.50 (m, 2H), 3.25 (s, 3H); HRMS m/z 400.1126 for $C_{20}H_{19}FN_3O_3S$ found 400.1123.

Other thiazole-containing compounds of the invention, such as compounds 1-29, are made by analogous procedures, substituting the appropriate benzonitrile in the first step, and the appropriate benzo[d]imidazol-2(3H-one, benzo[d]oxazol-2(3H)-one or indolinone starting materials in the final ring formation step, as would be evident to the person skilled in the art.

| Compound | 1H NMR | HRMS |
|---|---|---|
| 1 | 1H NMR (500 MHz, DMSO) δ 11.79 (s, 1H), 8.17 – 8.06 (m, 3H), 7.98 – 7.87 (m, 2H), 7.43 – 7.34 (m, 2H), 7.19 (d, J = 8.1 Hz, 1H). | HRMS: Found [M + H]+ 313.0446, C16H10FN2O2S requires 313.0441 |
| 2 | 1H NMR (500 MHz, DMSO) δ 11.72 (s, 1H), 7.91 (d, J = 1.3 Hz, 1H), 7.88 – 7.86 (m, 2H), 7.29 (dd, J = 10.1, 2.7 Hz, 1H), 7.21 – 7.16 (m, 2H), 2.64 (s, 3H). | HRMS: Found [M + H]+ 327.06149, C17H12FN2O2S requires 327.0598 |
| 3 | 1H NMR (500 MHz, DMSO) δ 10.51 (s, 1H), 8.05 (s, 1H), 7.94 – 7.81 (m, 3H), 7.29 (dd, J = 10.2, 2.7 Hz, 1H), 7.19 (td, J = 8.5, 2.8 Hz, 1H), 6.90 (d, J = 8.8 Hz, 1H), 3.56 (s, 2H), 2.64 (s, 3H). | HRMS: Found [M + H]+ 326.0753, C17H13FN3OS requires 326.0758 |
| 4 | 1H NMR (500 MHz, DMSO) δ 10.74 (s, 2H), 8.07 (s, 1H), 7.87 (dd, J = 8.6, 5.9 Hz, 1H), 7.67 – 7.50 (m, 2H), 7.34 – 7.15 (m, 2H), 7.01 (d, J = 8.1 Hz, 1H), 2.65 (s, 3H). | HRMS: Found [M + H]+ 325.0806, C18H14FN2OS requires 325.0805 |
| 5 | 1H NMR (500 MHz, DMSO) δ 11.81 (s, 1H), 8.18 (s, 1H), 7.89 (d, J = 1.4 Hz, 1H), 7.84 (dd, J = 8.1, 1.6 Hz, 1H), 7.75 (dd, J = 8.6, 5.9 Hz, 1H), 7.29 (dd, J = 10.2, 2.7 Hz, 1H), 7.21 – 7.17 (m, 2H), 3.00 (q, J = 7.5 Hz, 2H), 1.22 (t, J = 7.5 Hz, 3H). | HRMS: Found [M + H]+ 341.0754, C18H14FN2O2S requires 341.0755 |
| 6 | 1H NMR (500 MHz, DMSO) δ 11.74 (s, 1H), 8.23 (s, 1H), 7.94 (d, J = 1.3 Hz, 1H), 7.92 – 7.87 (m, 2H), 7.20 – 7.14 (m, 2H), 7.00 (dd, J = 10.7, 2.7 Hz, 1H), 2.54 – 2.44 (m, 1H), 1.05 (ddd, J = 8.4, 6.4, 4.3 Hz, 2H), 0.88 – 0.79 (m, 2H). | HRMS: Found [M + H]+ 353.0781, C19H14FN2O2S requires 353.0755 |
| 7 | 1H NMR (500 MHz, DMSO) δ 11.77 (s, 1H), 8.18 (s, 1H), 7.90 (d, J = 1.3 Hz, 1H), 7.85 (dd, J = 8.1, 1.5 Hz, 1H), 7.78 (dd, J = 8.5, 5.9 Hz, 1H), 7.30 – 7.21 (m, 2H), 7.17 (d, J = 8.1 Hz, 1H), 5.98 (ddt, J = 16.7, 10.1, 6.5 Hz, 1H), 5.07 – 4.92 (m, 2H), 3.83 (d, J = 6.4 Hz, 2H). | HRMS: Found [M + H]+ 353.0779, C19H14FN2O2S requires 353.0755 |
| 8 | 1H NMR (500 MHz, DMSO) δ 11.74 (s, 1H), 8.16 (s, 1H), 7.92 – 7.80 (m, 3H), 7.54 (dd, J = 10.5, 2.8 Hz, 1H), 7.25 (td, J = 8.4, 2.9 Hz, 1H), 7.18 (d, J = 8.1 Hz, 1H), 5.50 (s, 1H), 4.95 (s, 2H). | HRMS: Found [M + H]+ 343.0570, C17H12FN2O3S requires 343.0547 |
| 9 | 1H NMR (500 MHz, DMSO) δ 11.76 (s, 1H), 8.19 (s, 1H), 7.91 (d, J = 1.4 Hz, 1H), 7.84 (dd, J = 8.1, 1.6 Hz, 1H), 7.74 (dd, J = 8.6, 5.9 Hz, 1H), 7.29 (dd, J = 10.1, 2.7 Hz, 1H), 7.21 (td, J = 8.4, 2.8 Hz, 1H), | HRMS: Found [M +H]+ 357.0714, C18H14FN2O3S requires 357.0704 |

| Compound | 1H NMR | HRMS |
|---|---|---|
|  | 7.16 (d, J = 8.1 Hz, 1H), 4.73 (s, 1H), 3.69 (br. s, 2H), 3.15 (t, J = 6.9 Hz, 2H). |  |
| 10 | 1H NMR (500 MHz, DMSO) δ 11.74 (s, 1H), 8.17 (s, 1H), 7.90 – 7.84 (m, 2H), 7.79 (dd, J = 8.1, 1.6 Hz, 1H), 7.52 (dd, J = 10.2, 2.8 Hz, 1H), 7.39 – 7.24 (m, 6H), 7.16 (d, J = 8.1 Hz, 1H), 4.99 (s, 2H), 4.65 (s, 2H). | HRMS: Found [M + H]+ 433.1021, C24H18FN2O3S requires 433.1017 |
| 11 | 1H NMR (500 MHz, DMSO) δ 11.76 (s, 1H), 8.43 (td, J = 8.8, 6.5 Hz, 1H), 8.24 (s, 1H), 7.99 – 7.95 (m, 1H), 7.91 (dd, J = 8.1, 1.6 Hz, 1H), 7.51 (ddd, J = 11.7, 9.1, 2.5 Hz, 1H), 7.31 (td, J = 8.5, 2.5 Hz, 1H), 7.18 (d, J = 8.1 Hz, 1H) | HRMS: Found [M + H]+ 331.0350, C16H9F2N2O2S requires 331.0347 |
| 12 | 1H NMR (500 MHz, DMSO) δ 11.68 (s, 1H), 8.19 (s, 1H), 7.96 (dd, J = 8.8, 6.4 Hz, 1H), 7.93 (d, J = 1.4 Hz, 1H), 7.86 (dd, J = 8.1, 1.6 Hz, 1H), 7.48 (dd, J = 10.0, 2.6 Hz, 1H), 7.41 – 7.36 (m, 1H), 7.19 (d, J = 8.1 Hz, 1H), 6.00 (d, J = 47.8 Hz, 2H). | HRMS: Found [M + H]+ 345.0523, C17H11F2N2O2S requires 345.0509 |
| 13 | 1H NMR (500 MHz, DMSO) δ 8.19 (s, 1H), 7.90 (d, J = 1.4 Hz, 1H), 7.88 – 7.82 (m, 2H), 7.48 (dd, J = 10.2, 2.7 Hz, 1H), 7.27 (td, J = 8.4, 2.8 Hz, 1H), 7.18 (d, J = 8.1 Hz, 1H), 4.01 (s, 2H), 2.33 (s, 3H). | HRMS: Found [M + H]+ 356.0843, C18H15FN3O2S requires 356.0864 |
| 14 | 1H NMR (500 MHz, DMSO) δ 11.74 (s, 1H), 8.20 (s, 1H), 7.92 (d, J = 1.3 Hz, 1H), 7.89 – 7.83 (m, 2H), 7.42 (dd, J = 9.9, 2.1 Hz, 1H), 7.29 (td, J = 8.3, 2.2 Hz, 1H), 7.18 (d, J = 8.1 Hz, 1H), 3.79 (s, 2H), 2.18 (s, 6H). | HRMS: Found [M + H]+ 370.0996, C19H17FN3O2S requires 370.1020 |
| 15 | 1H NMR (500 MHz, DMSO) δ 11.67 (br. s, 1H), 8.17 (s, 1H), 7.88 (d, J = 1.4 Hz, 1H), 7.87 – 7.82 (m, 2H), 7.43 (dd, J = 10.1, 2.8 Hz, 1H), 7.28 (td, J = 8.4, 2.8 Hz, 1H), 7.15 (d, J = 8.1 Hz, 1H), 3.81 (s, 2H), 3.55 – 3.47 (m, 4H), 2.40 – 2.29 (m, 4H). | HRMS: Found [M + H]+ 412.1109, C21H19FN3O3S requires 412.1126 |
| 16 | 1H NMR (500 MHz, DMSO) δ 11.86 (s, 1H), 8.24 (s, 1H), 7.95 (d, J = 1.4 Hz, 1H), 7.87 (dd, J = 8.1, 1.6 Hz, 1H), 7.80 (dd, J = 8.6, 5.8 Hz, 1H), 7.43 (dd, J = 9.9, 2.7 Hz, 1H), 7.30 (td, J = 8.4, 2.7 Hz, 1H), 7.18 (d, J = 8.1 Hz, 1H), 4.17 – 4.04 (m, 2H), 3.47 – 3.39 (m, 2H), 3.16 (d, J = 4.8 Hz, 7 = 6H). | HRMS: Found [M + H]+ 384.1177, C20H19FN3O2S requires 384.1177 |
| 17 | 1H NMR (500 MHz, DMSO) δ 11.77 (s, 1H), 8.19 (s, 1H), 7.94 – 7.82 (m, 3H), 7.48 (dd, J = 10.3, 2.8 Hz, 1H), 7.29 (td, J = 8.4, 2.8 Hz, 1H), 7.18 (d, J = 8.1 Hz, 1H), 4.97 (s, 2H), 3.69 – 3.63 (m, 2H), 3.54 – 3.48 (m, 2H), 3.26 (s, 3H). | HRMS: Found [M + H]+ 401.1044, C20H18FN3O4S requires 401.0966 |
| 18 | 1H NMR (500 MHz, DMSO) δ 11.77 (s, 1H), 8.19 (s, 1H), 7.95 – 7.84 (m, 3H), 7.57 (dd, J = 10.4, 2.8 Hz, 1H), 7.29 (td, J = 8.4, 2.8 Hz, 1H), 7.19 (d, J = 8.2 Hz, 1H), 4.97 (s, 2H), 4.73 (d, J = 6.3 Hz, 1H), 3.57 (s, 2H). | HRMS: Found [M + H]+ 387.0818, C19H16FN2O4S requires 387.0809 |
| 19 | 1H NMR (500 MHz, DMSO) δ 11.86 (br. s, 1H), 8.22 (s, 1H), 8.04 (br. s, 2H), 7.94 (d, J = 1.5 Hz, 1H), 7.92 – 7.85 (m, 2H), 7.70 (dd, J = 10.4, 2.8 Hz, 1H), 7.32 (td, J = 8.4, 2.8 Hz, 1H), 7.20 (d, J = 8.1 Hz, 1H), 5.03 (s, 2H), 3.77 (t, J = 5.2 Hz, 2H), 3.09 (t, J = 5.0 Hz, 2H). | HRMS: Found [M + H]+ 386.0958, C19H17FN3O3S requires 386.0975 |
| 20 | 1H NMR (500 MHz, DMSO) δ 11.80 (br. s, | HRMS: Found [M + H]+ 440.1434, |

-continued

| Compound | 1H NMR | HRMS |
|---|---|---|
| | 1H), 9.58 (br. s, 1H), 8.22 (s, 1H), 7.94 (d, J = 1.5 Hz, 1H), 7.90 (dd, J = 8.7, 5.7 Hz, 1H), 7.87 (dd, J = 8.1, 1.6 Hz, 1H), 7.61 (dd, J = 10.3, 2.8 Hz, 1H), 7.33 (td, J = 8.4, 2.9 Hz, 1H), 7.19 (d, J = 8.1 Hz, 1H), 5.05 (s, 2H), 3.84 (app. br. s, 2H), 3.52 (app. br. s, 2H), 3.42 (app. br. s, 2H), 3.05 (app. br. s, 2H), 1.97 (app. br. s, 2H), 1.87 (app. br. s, 2H). | C23H23FN3O3S requires 440.1439 |
| 21 | 1H NMR (500 MHz, CDCl3) δ 8.59 (s, 1H), 7.79 (dd, J = 8.6, 5.8Hz, 1H), 7.70 (br s, 1H), 7.67 (dd, J = 8.1, 1.5 Hz, 1H), 7.48 (s, 1H), 7.10 (d, J = 8.2 Hz, 1H), 7.06 (d, J = 9.6, 2.5 Hz, 1H), 7.01 (ddd, J = 8.3, 8.2, 2.6 Hz, 1H), 4.07 (t, J = 7.1 Hz, 2H), 2.73 (t, J = 7.1 Hz, 2H), 2.70 (s, 3H), 2.38 (s, 6H). | HRMS: Found [M + H]+ 397.1491, C21H22FN4OS requires 397.1493 |
| 22 | 1H NMR (500 MHz, DMSO) δ 10.69 (s, 1H), 8.04 (s, 1H), 7.74 (dd, J = 8.6, 5.9 Hz, 1H), 7.62 (dd, J = 8.0, 1.6 Hz, 1H), 7.56 (d, J = 1.4 Hz, 1H), 7.28 (dd, J = 10.2, 2.7 Hz, 1H), 7.28 (ddd, J = 8.5, 8.4, 2.8 Hz, 1H), 6.99 (d, J = 8.1 Hz, 1H), 3.00 (q, J = 7.5 Hz, 2H), 1.22 (t, J = 7.5 Hz, 3H). | HRMS: Found [M + H]+ 340.0910, C18H15FN3OS requires 340.0914 |
| 23 | 1H NMR (500 MHz, DMSO) δ 11.76 (s, 1H), 8.12 (s, 1H), 7.99 (dd, J = 7.3, 1.6 Hz, 1H), 7.96 (d, J = 1.3 Hz, 1 H), 7.93 – 7.86 (m, 2H), 7.34 – 7.26 (m, 1H), 7.18 (d, J = 8.2 Hz, 1H). | HRMS: Found [M + H]+ 327.0607, C17H12FN2O2S requires 327.0598 |
| 24 | 1H NMR (500 MHz, DMSO) δ 11.74 (s, 1H), 8.17 (m, 1H), 8.10 (m, 1H), 7.96 (s, 1H), 7.90 (m, 2H), 7.60 (m, 1H), 7.21 – 7.13 (m, 1H). | HRMS: Found [M + H]+ 331.0350, C16H9F2N2O2S requires 331.0347 |
| 25 | 1H NMR (500 MHz, CDCl3) δ 8.08 (s, 1H), 7.83 – 7.79 (m, 2H), 7.59 (s, 1H), 7.11 (d, J = 8.2 Hz, 1H), 6.87 (d, J = 9.4Hz, 1H), 2.32 (s, 6H). | HRMS: Found [M + H]+ 341.0755, C18H14FN2O2S requires 341.0755 |
| 26 | 1H NMR (500 MHz, DMSO) δ 11.76 (s, 1H), 8.32 – 8.21 (m, 2H), 7.99 (d, J = 1.4 Hz, 1H), 7.92 (dd, J = 8.1, 1.6 Hz, 1H), 7.28 (t, J = 8.7 Hz, 1H), 7.19 (d, J = 8.2 Hz, 1 H), 2.28 (s, 3H). | HRMS: Found [M + H]+ 345.0517, C17H11F2N2O2S requires 345.0504 |
| 27 | 1H NMR (500 MHz, DMSO) δ 11.74 (s, 1H), 8.23 (s, 1H), 7.92 (d, J = 1.4 Hz, 1H), 7.86 (dd, J = 8.1, 1.5 Hz, 1H), 7.70 – 7.60 (m, 1H), 7.43 (dd, J = 18.1, 8.8 Hz, 1H), 7.18 (d, J = 8.1 Hz, 1H), 2.58 (d, J = 2.5 Hz, 3H). | HRMS: Found [M + H]+ 345.0535, C17H11F2N2O2S requires 345.0504 |
| 28 | 1H NMR (500 MHz, DMSO) δ 10.61 (s, 1H), 8.09 – 8.04 (m, 2H), 8.02 (s, 1H), 7.83 (s, 1H), 7.37 (t, J = 8.8 Hz, 2H), 6.96 (s, 1H), 3.58 (s, 2H). | HRMS: Found [M + H]+ 345.0264, C17H11ClFN2OS requires 345.0259 |
| 29 | 1H NMR (500 MHz, DMSO) δ 10.62 (s, 1H), 8.36 (dd, J = 15.4, 8.7 Hz, 1H), 8.16 (s, 1H), 7.85 (s, 1H), 7.59 – 7.49 (m, 1H), 7.35 – 7.28 (m, 1H), 6.97 (s, 1H), 3.58 (s, 2H). | HRMS: Found [M + H]+ 363.0197, C17H10ClF2N2OS requires 363.0170 |
| 32 | 1H NMR (500 MHz, DMSO) d 10.79 – 10.72 (m, 2H), 8.06 (s, 1H), 7.87 (dd, J = 8.6, 5.6 Hz, 1H), 7.64 (dd, J = 8.1, 1.7 Hz, 2H), 7.57 (d, J = 1.7 Hz, 1H), 7.48 (dd, J = 10.3, 2.8 Hz, 1H), 7.29 (td, J = 8.4, 2.8 Hz, 1H), 7.00 (d, J = 8.1 Hz, 1H), 4.96 (s, 2H), 3.68 – 3.60 (m, 2H), 3.55 – 3.47 (m, 2H), 3.25 (s, 4H). | HRMS: Found [M + H]+ 400.1123, C20H19FN3O3S requires 400.1126 |

Synthesis 2

Pyridine Synthesis

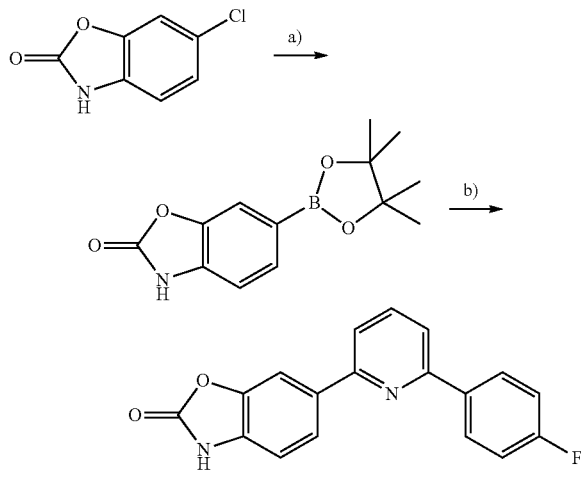

a) Bis(pinacolato)diboron, KOAc, Cy$_3$P, tris(dibenzylideneacetone)dipalladium(0), Dioxane, 100° C. to RT, 32%; b) 2-bromo-6-(4-fluorophenyl)pyridine, K$_2$CO$_3$, Pd(PPh$_3$)$_4$, RT, 81%

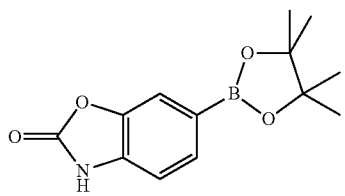 [SMILES: CC1(C)OB(c2ccc3[nH]c(=O)oc3c2)OC1(C)C]

6-(4,4,5,5-tetramethyl-1,3,2-dioxaborolan-2-yl) benzo[d]oxazol-2(3H)-one

A solution of 6-chloro-2-benzoxazolinone (2.50 g, 14.7 mmol), bis(pinacolato)diboron (4.44 g, 17.5 mmol), potassium acetate (2.21 g, 22.5 mmol) and tricyclohexylphosphine (0.60 g, 2.1 mmol) in 1,4-dioxane (15 mL) was bubbled through with nitrogen for 5 minutes before adding tris(dibenzylideneacetone)dipalladium(0) (0.81 g, 0.9 mmol). The mixture was further bubbled through with nitrogen for 15 minutes before heating to 100° C. in a sealed tube under nitrogen environment for 4 hours. The mixture was allowed to cool and the volatile was evaporated under vacuo. The resulting residue was partitioned with dichloromethane and water. The separated organic layer was washed, sequentially, with saturated sodium bicarbonate and saturated brine solutions, then dried over sodium sulfate. The mixture was filtered and the filtrate was evaporated to dryness in vacuo. The resulting residue was purified by chromatography using 5% ethyl acetate in dichloromethane to afford the titled compound as light brown solid (1.23 g, 32%). $^1$H NMR (400 MHz, DMSO) δ 11.75 (br. s, 1H), 7.47 (dd, J=1.09, 7.77, 1H), 7.39 (s, 1H), 7.08 (d, J=7.90, 1H), 1.27 (s, 12H).

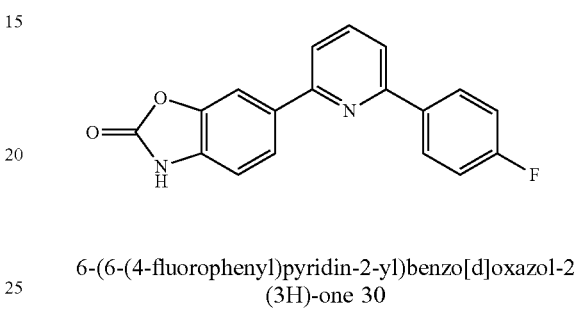

6-(6-(4-fluorophenyl)pyridin-2-yl)benzo[d]oxazol-2 (3H)-one 30

To a solution of 6-(4,4,5,5-tetramethyl-1,3,2-dioxaborolan-2-yl)benzo[d]oxazol-2(3H)-one (0.094 g, 0.323 mmol) in degassed Dioxane (3.23 ml) and water (9:1) was added 2-bromo-6-(4-fluorophenyl)pyridine (0.114 g, 0.484 mmol; CAS Registry No. 1142196-75-5; obtained from Combiphos Catalysts, Inc.), K$_2$CO$_3$ (0.223 g, 1.615 mmol) and Pd(PPh$_3$)$_4$ (0.019 g, 0.016 mmol) and the mixture was heated to 70° C. overnight under N$_2$. After this time, the mixture was cooled to room temperature, diluted with EtOAc washed with brine, dried (MgSO$_4$) and the solvent removed under reduced pressure to give a yellow oil which was purified by chromatography eluting with DCM:EtOAc (95:5) to give the title compound as a white solid in 20% yield. $^1$H NMR (500 MHz, DMSO) δ 11.83 (s, 1H), 8.31-8.27 (m, 2H), 8.15 (d, J=1.5 Hz, 1H), 8.08 (dd, J=8.2, 1.7 Hz, 1H), 7.98-7.90 (m, 3H), 7.37 (dd, J=8.9, 8.8 Hz, 2H), 7.23 (d, J=8.2 Hz, 1H). HRMS. Found [M+H]+307.0869, C$_{18}$H$_{12}$FN$_2$O$_2$ requires 307.0877.

Other pyridine-containing compounds of the invention, such as compound 31, are made by analogous procedures, substituting the appropriate halo-substituted benzo[d]imidazol-2(3H)-one, benzo[d]oxazol-2(3H)-one or indolinone in the boronic acid formation step, and the appropriate phenyl-substituted pyridine starting material in the coupling step, as would be evident to the person skilled in the art.

| Compound | 1H NMR | HRMS |
|---|---|---|
| 30 | 1H NMR (500 MHz, DMSO) δ 11.83 (s, 1H), 8.31 – 8.27 (m, 2H), 8.15 (d, J = 1.5 Hz, 1H), 8.08 (dd, J = 8.2, 1.7 Hz, 1H), 7.98 – 7.90 (m, 3H), 7.37 (dd, J = 8.9, 8.8 Hz, 2H), 7.23 (d, J = 8.2 Hz, 1H). | HRMS: Found [M + H]+ 307.0869, C18H12FN2O2 requires 307.0877 |
| 31 | 1H NMR (500 MHz, DMSO) δ 11.79 (s, 1H), 8.01 (d, J = 1.4 Hz, 1H), 7.98 (dd, J = 8.2, 1.6 Hz, 1H), 7.96 – 7.91 (m, 2H), 7.53 (dd, J = 8.5, 6.2 Hz, 1H), 7.48 – 7.43 (m, 1H), 7.23 – 7.18 (m, 2H), 7.15 (td, J = 8.5, 2.5 Hz, 1H), 2.42 (s, 3H). | HRMS: Found [M + H]+ 321.1029, C19H14FN2O2 requires 321.1034 |

Biological Methods

All cell lines were obtained from ATCC except KPL1 which was obtained from Leibniz Institute DSMZ-German Collection of Microorganisms and Cell Cultures, and SMOV2 which was obtained from Dr. Hiroaki Itamochi (Tottori University School of Medicine, Yonago, Japan; see also: 'Establishment and characterization of human ovarian clear cell adenocarcinoma cell line (SMOV-2), and its cytotoxity by anticancer agents', Yonamine K at al., *Hum Cell.*, 1999, 12(3), 139-48; and 'PPM1D Is a Potential Therapeutic Target in Ovarian Clear Cell Carcinoma', David S. P. Tan et al., *Clin Cancer Res,* 2009, 15, 2269).

3 Day/5 Day SRB Proliferation Assay:

Representative compounds were assessed in a sulforhodamine B (SRB) proliferation assay in the cell lines shown in the Tables below, according to the following general procedure:

Cells were seeded in a 96 well plate at a number optimized for each cell line as known in the art; for example as described in Viachai et al, Nature Protocols, 2006, 1 1112-1116. Two fold dilutions of the compounds to be tested were made in culture medium so that, when diluted 5×, the final concentration in the wells was from 50 μM to 0.000191 μM (19 concentrations). A day after seeding the cells in 96 well plates, 25 μl of the compound diluted in the culture medium was added to 100 μl of the cells and incubated at 37° C. and 5% $CO_2$ for 3 or 5 more days as required. After this time, cells were fixed by adding 10% ice cold TCA (in $H_2O$) to 3% final concentration in the wells and by incubating at 4° C. for at least 2 h. Plates were washed 4 times in $H_2O$ and allowed to dry in the air. Added 100 μl of 0.057% SRB solution to the dried plates and incubated at room temperature for at least 30 min. Removed SRB solution from the plates and washed four times with 1% acetic acid. Plates were left overnight to dry in the air followed by addition of 100 μl of 10 mM Tris pH 10.5 to each well of the dried plates and incubation on a shaker for 5 min to solubilize the SRB. Optical density was measured at wave length of 490 nm using a plate reader and analysis performed to measure the GI50 using GraphPad PRISM.

Western Blot Analysis:

Biomarker modulation by representative compounds was assessed by Western blot analysis in SMOV2 cells using the following procedure:

On day one, $3 \times 10^5$ cells were plated per well in a 6 well plate. Next day cells were treated with DMSO control or indicated concentrations of the representative compounds for 24 hours. Treated cells were lysed in complete lysis buffer (50 mM NaCl, 20 mM Tris pH7.5, 1 mM EDTA, 1 mM EGTA, 1% Triton X100, 10 mM NaF, protease Inhibitor tablet and phosphatase inhibitor cocktails) on ice for 10 min. Soluble proteins were separated by centrifugation, and protein concentration was measured using Bradford assay. Samples with equal amount of proteins were prepared and run on LDS-PAGE. Separated proteins were transferred to the nitrocellulose membrane and probed with the Phospho-p38, Phospho-p53 S15, cleaved PARP, γ-H2AX and GAPDH antibodies.

Biological Data

Example 1

PP1MD Amplified Cell Lines (A) Vs. Control (NA)

TABLE 1

| Compound # | GI50 3-day SMOV2 (A) SRB (nM) | GI50 5-day SMOV2 (A) SRB (nM) | GI50 5-day TOV21G (NA) SRB (nM) |
|---|---|---|---|
| 1 | 9 | 1.1 | >10000 |
| 2 | 1.6 | 0.5 | >10000 |
| 3 | 1.2 | 0.5 | >10000 |
| 4 | 0.2 | 0.1 | >10000 |
| 5 | 13 | 9.7 | >10000 |
| 6 | 200 | — | — |
| 7 | 77 | — | — |
| 8 | 23 | 0.1 | 9200 |
| 9 | 7 | 0.6 | >10000 |
| 10 | 300 | | |
| 11 | 7 | 0.75 | >10000 |
| 12 | 2 | 0.3 | 5200 |
| 13 | 32 | 6 | 1600 |
| 14 | 10 | 2 | 1600 |
| 15 | 520 | — | — |
| 16 | 40 | 6 | 9200 |
| 17 | 1.2 | 0.1 | 9400 |
| 18 | 1.7 | 0.9 | 9500 |
| 19 | 1.4 | 5 | 1200, 1700 |
| 20 | 13 | 11 | 1500 |
| 21 | 8 | 0.1 | 7200 |
| 22 | 0.38 | 0.2 | 660 |
| 23 | 250 | — | — |
| 24 | 290 | — | — |
| 25 | 500 | — | — |
| 26 | >10000 | — | — |
| 27 | 1.2 | 0.2 | >10000 |
| 28 | 93 | — | — |
| 29 | 1900 | — | — |
| 30 | 280 | 35 | 2700 |
| 31 | >10000 | — | — |
| 32 | 4.8 | 1.6 | >10000 |

TABLE 2

Additional Cell Lines

| Compound # | GI50 5-Day MCF7 (A) SRB (nM) | GI50 5-Day KPL1 (A) SRB (nM) | GI50 5-Day MDAMB231 (NA) SRB (nM) | GI50 5-Day HeLa (NA) SRB (nM) | GI50 5-Day Cama1 (NA) SRB (nM) |
|---|---|---|---|---|---|
| 32 | 4.6 | 36 | >10000 | 5600 | 3900 |

Example 2

Western Blot Analysis

Compound 32 was analysed according to the general procedure described above to assess biomarker modulation in SMOV2 cells. The results are depicted in FIG. 1.

These results show modulation of the biomarkers expected for PP1MD-mediated inhibition.

The invention claimed is:

1. A compound of formula (Ia) or a pharmaceutically acceptable salt thereof:

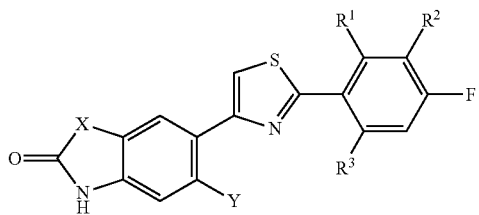

wherein:
X is O;
Y is selected from H, F, and Cl;
$R^1$ is selected from H, F, cyclopropyl, and —$CH_2$—$Z^B$, wherein $Z^B$ is selected from:
  H, F, Cl, Me, —CH=$CH_2$,
  —$OR^{B1}$, —$NR^{B1}R^{B2}$,
  -$L^{B1}$-$OR^{B1A}$, -$L^{B1}$-$NR^{B1A}R^{B1B}$,
  —O-$L^{B2}$-$OR^{B2A}$, —O-$L^{B2}$-$NR^{B2A}R^{B2B}$,
  —NH-$L^{B2}$-$OR^{B2A}$, and —NH-$L^{B2}$-$NR^{B2A}R^{B2B}$, wherein:
$R^{B1}$ and $R^{B2}$ are each independently H or $C_{1-4}$alkyl,
$L^{B1}$ is $C_{1-3}$ alkylene,
$R^{B1A}$ and $R^{B1B}$ are each independently H or $C_{1-4}$alkyl,
and $L^{B2}$ is $C_{1-3}$ alkylene, and
$R^{B2A}$ and $R^{B2B}$ are each independently H or $C_{1-4}$alkyl;
$R^2$ is selected from H, F, and Me; and
$R^3$ is selected from H, F and Me.

2. A compound according to claim 1, wherein Y is H.
3. A compound according to claim 1, wherein $R^1$ is selected from H and —$CH_2$—$Z^B$.
4. A compound according to claim 1, wherein $Z^B$ is selected from H, F, Cl, Me, and —CH=$CH_2$.
5. A compound according to claim 1, wherein $R^2$ is H.
6. A compound according to claim 1, wherein $R^3$ is H.
7. A compound according to claim 1, which is a compound selected from the following compounds and pharmaceutically acceptable salts thereof:

| Compound Ref | Structure | IUPAC Name |
|---|---|---|
| 1 | 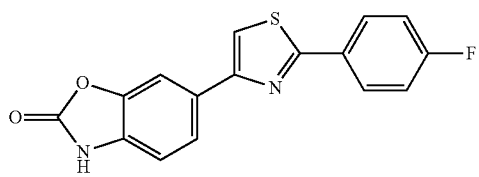 [SMILES: O=c1[nH]c2ccc(-c3csc(-c4ccc(F)cc4)n3)cc2o1] | 6-(2-(4-fluorophenyl)thiazol-4-yl)benzo[d]oxazol-2(3H)-one |
| 2 | 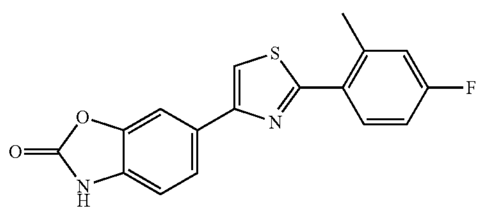 [SMILES: Cc1cc(F)ccc1-c1nc(-c2ccc3[nH]c(=O)oc3c2)cs1] | 6-(2-(4-fluoro-2-methylphenyl)thiazol-4-yl)benzo[d]oxazol-2(3H)-one |
| 5 | 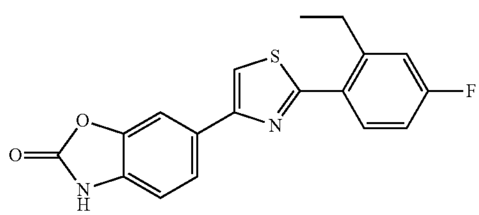 [SMILES: CCc1cc(F)ccc1-c1nc(-c2ccc3[nH]c(=O)oc3c2)cs1] | 6-(2-(2-ethyl-4-fluorophenyl)thiazol-4-yl)benzo[d]oxazol-2(3H)-one |
| 6 | 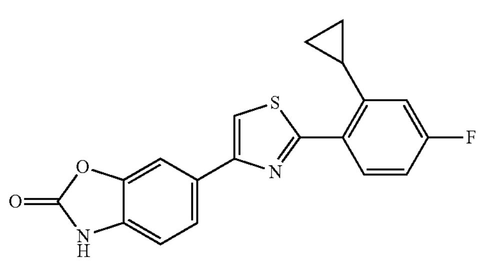 [SMILES: O=c1[nH]c2ccc(-c3csc(-c4ccc(F)cc4C4CC4)n3)cc2o1] | 6-(2-(2-cyclopropyl-4-fluorophenyl)thiazol-4-yl)benzo[d]oxazol-2(3H)-one |
| 7 | 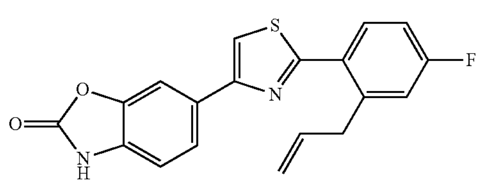 [SMILES: C=CCc1cc(F)ccc1-c1nc(-c2ccc3[nH]c(=O)oc3c2)cs1] | 6-(2-(2-allyl-4-fluorophenyl)thiazol-4-yl)benzo[d]oxazol-2(3H)-one |

-continued

| Compound Ref | Structure | IUPAC Name |
|---|---|---|
| 8 | 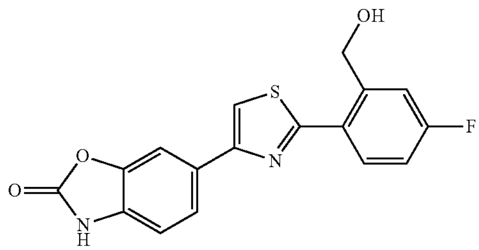 [SMILES: O=c1[nH]c2ccc(-c3csc(-c4ccc(F)cc4CO)n3)cc2o1] | 6-(2-(4-fluoro-2-(hydroxymethyl)phenyl)thiazol-4-yl)benzo[d]oxazol-2(3H)-one |
| 9 | 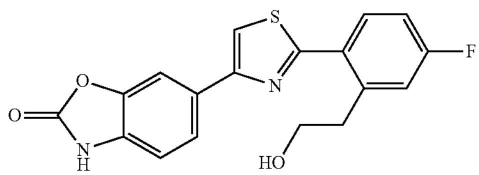 [SMILES: O=c1[nH]c2ccc(-c3csc(-c4ccc(F)cc4CCO)n3)cc2o1] | 6-(2-(4-fluoro-2-(2-hydroxyethyl)phenyl)thiazol-4-yl)benzo[d]oxazol-2(3H)-one |
| 10 | 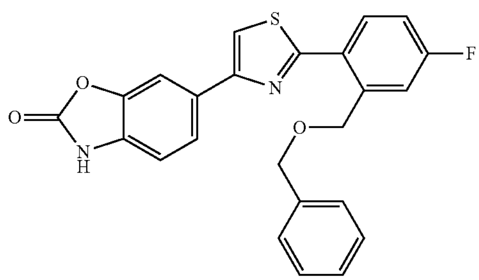 [SMILES: O=c1[nH]c2ccc(-c3csc(-c4ccc(F)cc4COCc4ccccc4)n3)cc2o1] | 6-(2-(2-((benzyloxy)methyl)-4-fluorophenyl)thiazol-4-yl)benzo[d]oxazol-2(3H)-one |
| 11 | 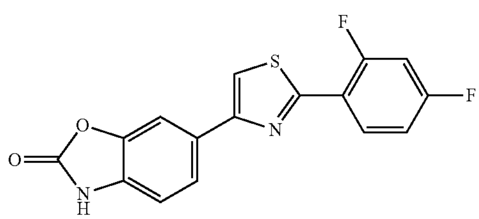 [SMILES: O=c1[nH]c2ccc(-c3csc(-c4ccc(F)cc4F)n3)cc2o1] | 6-(2-(2,4-difluorophenyl)thiazol-4-yl)benzo[d]oxazol-2(3H)-one |
| 12 | 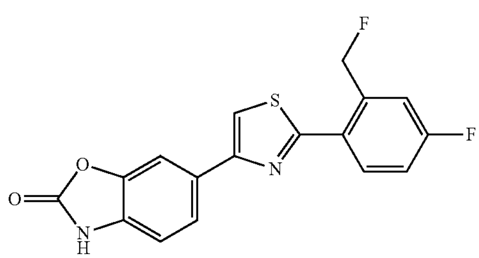 [SMILES: O=c1[nH]c2ccc(-c3csc(-c4ccc(F)cc4CF)n3)cc2o1] | 6-(2-(4-fluoro-2-(fluoromethyl)phenyl)thiazol-4-yl)benzo[d]oxazol-2(3H)-one |
| 13 | 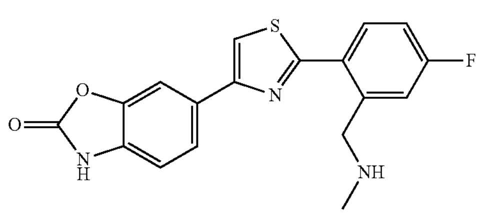 [SMILES: CNCc1cc(F)ccc1-c1nc(-c2ccc3[nH]c(=O)oc3c2)cs1] | 6-(2-(4-fluoro-2-((methylamino)methyl)phenyl)thiazol-4-yl)benzo[d]oxazol-2(3H)-one |

-continued

| Compound Ref | Structure | IUPAC Name |
|---|---|---|
| 14 | 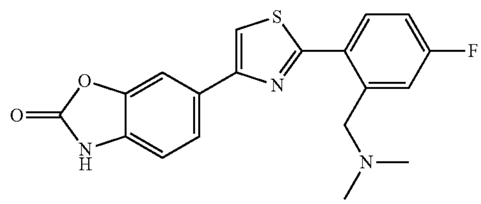 [SMILES: CN(C)Cc1cc(F)ccc1-c1nc(-c2ccc3[nH]c(=O)oc3c2)cs1] | 6-(2-(2-((dimethylamino)methyl)-4-fluorophenyl)thiazol-4-yl)benzo[d]oxazol-2(3H)-one |
| 16 | 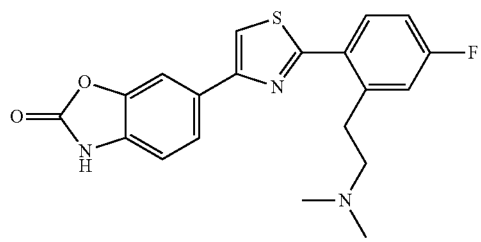 [SMILES: CN(C)CCc1cc(F)ccc1-c1nc(-c2ccc3[nH]c(=O)oc3c2)cs1] | 6-(2-(2-(2-(dimethylamino)ethyl)-4-fluorophenyl)thiazol-4-yl)benzo[d]oxazol-2(3H)-one |
| 17 | 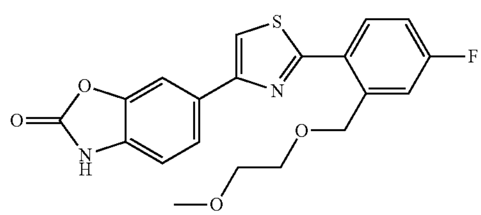 [SMILES: COCCOCc1cc(F)ccc1-c1nc(-c2ccc3[nH]c(=O)oc3c2)cs1] | 6-(2-(4-fluoro-2-((2-methoxyethoxy)methyl)phenyl)thiazol-4-yl)benzo[d]oxazol-2(3H)-one |
| 18 | 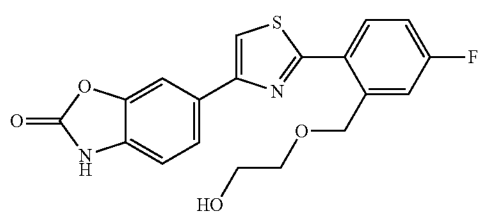 [SMILES: O=c1[nH]c2ccc(-c3csc(-c4ccc(F)cc4COCCO)n3)cc2o1] | 6-(2-(4-fluoro-2-((2-hydroxyethoxy)methyl)phenyl)thiazol-4-yl)benzo[d]oxazol-2(3H)-one |
| 19 | 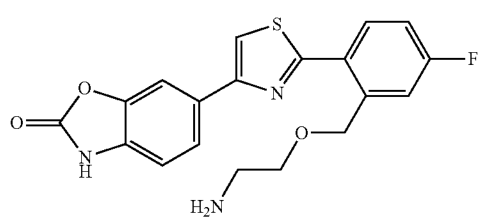 [SMILES: NCCOCc1cc(F)ccc1-c1nc(-c2ccc3[nH]c(=O)oc3c2)cs1] | 6-(2-(2-((2-aminoethoxy)methyl)-4-fluorophenyl)thiazol-4-yl)benzo[d]oxazol-2(3H)-one |
| 23 | 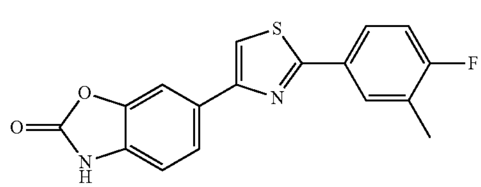 [SMILES: Cc1cc(-c2nc(-c3ccc4[nH]c(=O)oc4c3)cs2)ccc1F] | 6-(2-(4-fluoro-3-methylphenyl)thiazol-4-yl)benzo[d]oxazol-2(3H)-one |
| 24 | 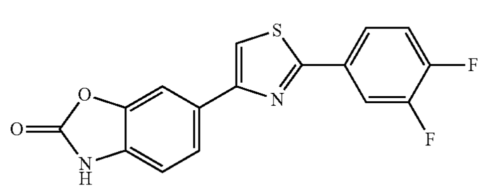 [SMILES: O=c1[nH]c2ccc(-c3csc(-c4ccc(F)c(F)c4)n3)cc2o1] | 6-(2-(3,4-difluorophenyl)thiazol-4-yl)benzo[d]oxazol-2(3H)-one |

| Compound Ref | Structure | IUPAC Name |
|---|---|---|
| 25 | 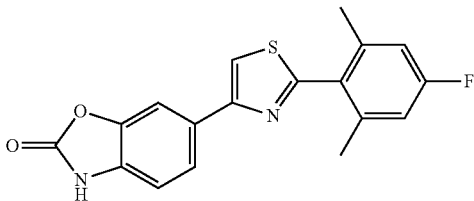 [SMILES: Cc1cc(F)cc(C)c1-c1nc(-c2ccc3[nH]c(=O)oc3c2)cs1] | 6-(2-(4-fluoro-2,6-dimethylphenyl)thiazol-4-yl)benzo[d]oxazol-2(3H)-one |
| 26 | 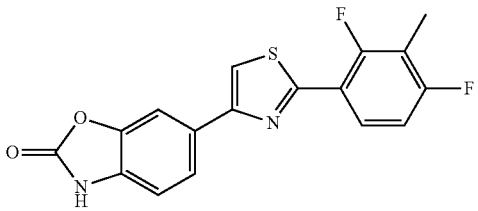 [SMILES: Cc1c(F)ccc(-c2nc(-c3ccc4[nH]c(=O)oc4c3)cs2)c1F] | 6-(2-(2,4-difluoro-3-methylphenyl)thiazol-4-yl)benzo[d]oxazol-2(3H)-one |
| 27 | 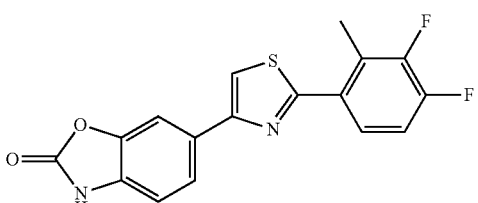 | 6-(2-(3,4-difluoro-2-methylphenyl)thiazol-4-yl)benzo[d]oxazol-2(3H)-one. |

8. A pharmaceutical composition comprising a compound according to claim 1 and a pharmaceutically acceptable carrier, diluent, or excipient.

9. A compound according to claim 1 wherein Y is H, $R^2$ is H, and $R^3$ is H.

10. A compound according to claim 1 wherein $R^1$ is —$CH_2$—$Z^B$, and wherein $Z^B$ is selected from —$OR^{B1}$, —$NR^{B1}R^{B2}$, -$L^{B1}$-$OR^{B1A}$, -$L^{B1}$-$NR^{B1A}R^{B1B}$, -$L^{B1}$-$OR^{B1A}$, -$L^{B1}$-$NR^{B1A}R^{B1B}$, $L^{B1}$-$R^{B1C}$, —O-$L^{B2}$-$OR^{B2A}$, —O-$L^{B2}$-$NR^{B2A}R^{B2B}$, —O-$L^{B2}$-$R^{B2C}$, —NH-$L^{B2}$-$OR^{B2A}$, —NH-$L^{B2}$-$NR^{B2A}R^{B2B}$ and —NH-$L^{B2}$-$R^{B2C}$.

11. A compound according to claim 1 wherein $R^1$ is —$CH_2$—$Z^B$ and wherein $Z^B$ is —O-$L^{B2}$-$OR^{B2A}$.

12. A compound according to claim 1 wherein $R^1$ is —$CH_2$—$Z^B$ and wherein $Z^B$ is —O—$CH_2CH_2$—O-Me.

13. A compound according to claim 1 which is a compound of formula

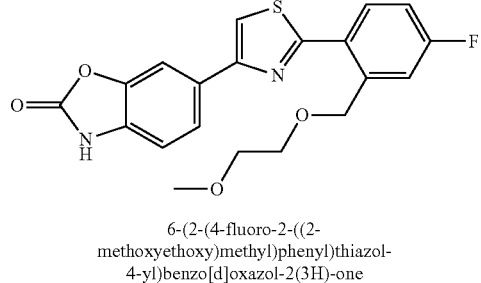 [SMILES: COCCOCc1cc(F)ccc1-c1nc(-c2ccc3[nH]c(=O)oc3c2)cs1]

6-(2-(4-fluoro-2-((2-methoxyethoxy)methyl)phenyl)thiazol-4-yl)benzo[d]oxazol-2(3H)-one or a pharmaceutically acceptable salt thereof.

* * * * *